United States Patent
Ingham et al.

(10) Patent No.: US 9,901,450 B2
(45) Date of Patent: Feb. 27, 2018

(54) COMPOSITE BONE IMPLANTS

(71) Applicant: University of Leeds, Leeds Yorkshire (GB)

(72) Inventors: Eileen Ingham, Leeds (GB); Gemma Jones, Leeds (GB); Hazel Fermor, Leeds (GB); John Fisher, Leeds (GB); Jahid Hasan, Leeds (GB)

(73) Assignee: University of Leeds (GB)

( * ) Notice: Subject to any disclaimer, the term of this patent is extended or adjusted under 35 U.S.C. 154(b) by 0 days.

(21) Appl. No.: 14/425,234

(22) PCT Filed: Sep. 4, 2013

(86) PCT No.: PCT/GB2013/052312
§ 371 (c)(1),
(2) Date: Mar. 2, 2015

(87) PCT Pub. No.: WO2014/037713
PCT Pub. Date: Mar. 13, 2014

(65) Prior Publication Data
US 2015/0216664 A1    Aug. 6, 2015

(30) Foreign Application Priority Data
Sep. 4, 2012 (GB) .................................. 1215725.1

(51) Int. Cl.
    *A61F 2/08*     (2006.01)
    *A61F 2/28*     (2006.01)
    *A61L 27/36*     (2006.01)

(52) U.S. Cl.
CPC .............. *A61F 2/28* (2013.01); *A61L 27/365* (2013.01); *A61L 27/3608* (2013.01);
(Continued)

(58) Field of Classification Search
CPC .... A61F 2/08; A61L 27/3683; A61L 27/3608; A61L 27/3965
See application file for complete search history.

(56) References Cited

U.S. PATENT DOCUMENTS

| | | | |
|---|---|---|---|
| 5,513,662 A | 5/1996 | Morse et al. | |
| 2010/0152852 A1* | 6/2010 | Ingham | A61F 2/3872 623/14.12 |

(Continued)

FOREIGN PATENT DOCUMENTS

| | | |
|---|---|---|
| CN | 101332314 B | 11/2012 |
| GB | 2443938 A | 5/2008 |

(Continued)

OTHER PUBLICATIONS

Notification of Transmittal of the International Search Report and the Written Opinion of the International Searching Authority, or the Declaration corresponding to International Application No. PCT/GB2013/052312 mailed Nov. 27, 2013.

(Continued)

*Primary Examiner* — Brian Dukert
(74) *Attorney, Agent, or Firm* — Ward and Smith, P.A.

(57) ABSTRACT

The invention provides natural multi-composite bone implants such as bone-connective tissue-bone and osteochondral implants for the replacement and/or repair of, for example and in particular a damaged or defective bone-meniscus-bone joint or a bone-patella tendon-bone joint or osteochondral lesions, methods of preparing the composites and uses thereof. The invention also provides natural or native composite bone-connective tissue-bone and osteochondral matrices or scaffolds that are substantially decellularized for subsequent transplantation/implantation.

12 Claims, 19 Drawing Sheets

(52) U.S. Cl.
    CPC ....... *A61L 27/3687* (2013.01); *A61L 27/3691* (2013.01); *A61F 2210/0085* (2013.01); *A61L 2430/02* (2013.01); *A61L 2430/40* (2013.01)

(56) References Cited

U.S. PATENT DOCUMENTS

| | | | |
|---|---|---|---|
| 2011/0143438 | A1 | 6/2011 | Wolfinbarger, Jr. et al. |
| 2014/0350677 | A1* | 11/2014 | Chang ................. A61L 27/3683 623/13.17 |

FOREIGN PATENT DOCUMENTS

| | | |
|---|---|---|
| JP | 2010-509965 A | 4/2010 |
| WO | WO 98/46165 A1 | 10/1998 |
| WO | WO 2008/059244 | 5/2008 |
| WO | WO 2008/111530 A1 | 9/2008 |
| WO | WO 2011/132089 A2 | 10/2011 |
| WO | WO 2011/142407 A2 | 11/2011 |

OTHER PUBLICATIONS

Search Report corresponding to British Application No. GB1215725.1 dated Dec. 17, 2012 (6 pages).
Search Report corresponding to British Application No. GB1315709.4 dated Mar. 5, 2014 (3 pages).
Notification of Reasons for Refusal, Japanese Patent Application No. 2015-529129; Dispatch Date: Dec. 6, 2016, 5 pages.
Qiang et al., "Fabrication and characterization of a novel acellular bone matrix scaffold for bone tissue engineering," Journal of Clinical Rehabilitative Tissue Engineering Research, vol. 15, No. 38, Sep. 17, 2011, pp. 7041-7044.
Notification of Reasons for Refusal, Japanese Patent Application No. 2015-529129; dated Dec. 6, 2016, 5 pages.
Woods et al., "Effectiveness of three extraction techniques in the development of a decellularized bone-anterior cruciate ligament-bone graft.", Biomaterials. 2005;26(35):7339-49.

* cited by examiner

| ECM Component | Fresh | | | | Decellularised | | | |
|---|---|---|---|---|---|---|---|---|
| | Inner | Outer | Attach | Bone | Inner | Outer | Attach | Bone |
| Collagen I | ++ | +++ | +++ | +++ | + | ++ | +++ | +++ |
| Collagen II | +++ | + | ++ | ++ | +++ | + | ++ | ++ |
| Collagen III | ++ | ++ | ++ | ++ | ++ | ++ | + | ++ |
| Collagen IV | + | ++ | + | ++ | - | - | - | - |
| Collagen VI | + | ++ | ++ | ++ | +/- | +/- | +/- | ++ |
| Osteocalcin | n/a | n/a | n/a | ++ | n/a | n/a | n/a | ++ |

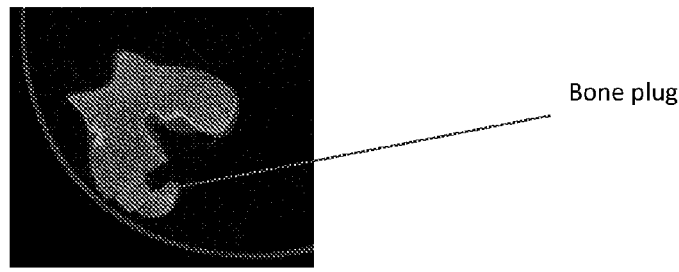
Figure 29
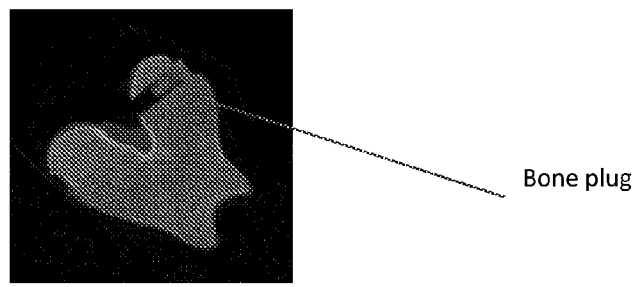
Figure 30
Figure 31
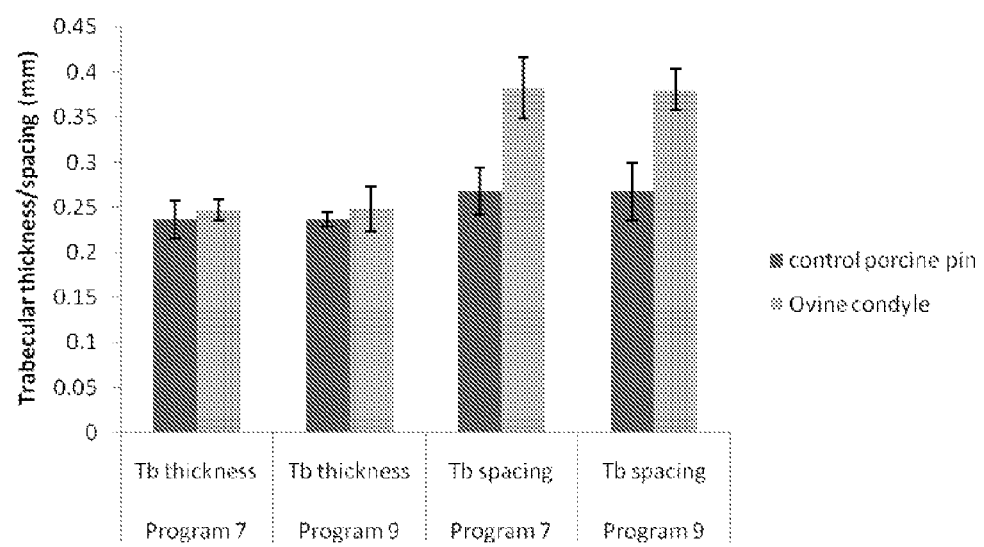

COMPOSITE BONE IMPLANTS

RELATED APPLICATIONS

This application is a 35 U.S.C. § 371 national stage application of PCT Application No. PCT/GB2013/052312, filed on Sep. 4, 2013, which claims priority from British Application No. 1215725.1, filed on Sep. 4, 2012, the contents of each are incorporated herein by reference in their entirety. The above-referenced PCT Application was published as International Publication No. WO 2014/037713 A1 on Mar. 13, 2014.

This invention relates to natural or native composite bone-connective tissue-bone implants and osteochondral grafts for the replacement and/or repair of, for example and in particular without limitation, a damaged or defective bone-meniscus-bone joint or a bone-ligament-bone attachment or osteochondral lesion, methods of preparing the bone-connective tissue-bone composites and uses thereof. The invention also provides natural or native composite bone-connective tissue-bone matrices and osteochondral matrices or scaffolds that are substantially decellularised for subsequent transplantation or implantation.

BACKGROUND

The knee joint is the largest and most complex joint in the human body. Owing to its anatomical structure it is susceptible to injury and damage through wear and tear. The menisci reside within this joint and play a vital role in joint stability, shock absorption and load transmission. Hence, injury to the menisci leads to altered joint biomechanics, and coupled with an inability to heal due to its avascularity, this leads in turn leads to subsequent degeneration of surrounding tissues characteristic of osteoarthritis (OA). There are approximately one million procedures related to the meniscus every year in the United States alone, and current treatment options only delay the onset of OA and do not provide a cure. Therefore, a meniscal replacement is necessary in order to halt the progression of OA and restore native joint biomechanics. Treatment depends on the severity of a tear and the age and health status of the patient, typical treatments include a total meniscectomy where the entire meniscus is removed, a partial meniscectomy where the surgeon removes as little of the meniscus as possible and any unstable meniscal fragments are removed with the remaining meniscus edges smoothed so that there are no frayed ends. Alternatively the tear can be repaired by sutures or the like, however not all tears can be repaired in this way and even if they can this method can cause injury to the surrounding tissue or create inferior fibrous scar tissue formed in outer tears that heal. A yet further option is that the meniscus can be totally replaced by, for example, a collagen meniscal implant composed of collagen I or some other unorganized matrix or by a knee joint prosthesis. Many avenues have been investigated in the search for a meniscal replacement, from autogenous, allogeneic and xenogeneic tissue sources, to more recent tissue engineering strategies. A limitation of allografts is their tissue availability, potential for disease transmission, their overall tissue quality and the possibility of tissue rejection. A limitation of xenogeneic tissue is how to achieve biocompatibility and immunologically inert tissue.

The meniscus comprises four different and distinct cell populations; (i) endothelial cells reside in the vasculature (ii) fusiform cells populate the superficial region; (iii) rounded cells are found in the hyaline-like region and; (iv) fibroblast-like cells are found deep within the central region, the presence of deeply embedded cells is one of the reasons why historically decellularisation of allogenic and xenogeneic tissue sources has proven difficult to achieve. WO 2008/059244 describes a method of decellularising meniscal tissue.

Ligaments connect bones to other bones to form a joint, some ligaments limit the mobility of articulations, or prevent certain movements altogether. Ligaments are mechano-responsive, mechanically strong and viscoelastic. Ligaments gradually lengthen when under tension, and return to their original shape when the tension is removed. However, they cannot retain their original shape when stretched past a certain point or for a prolonged period of time. This is one reason why dislocated joints must be set as quickly as possible: if the ligaments lengthen too much, then the joint will be weakened, becoming prone to future dislocations. Ligament injuries are relatively common both in man and animals for example in 2005 a study estimated that $1.32 billion was spent in the United States in treating the cranial cruciate ligament of dogs. In humans, ligament injuries are more common in the knee joint which frequently affects the cruciate ligaments. Ligament injuries can be divided into two types, acute and chronic injury. Ruptures are the most common acute form and often occur in sports settings. The complete division or detachment of a ligament causes immediate loss of its function, which is permanent unless it is repaired. Chronic ligament injury is manifested by pain and swelling. Ligaments are soft connective tissue that are composed of: closely packed parallel collagen fibre bundles; ligament fibroblasts which are the dominant cells responsible for ligament homeostasis and repair and; stem cells which play a vital role in maintenance and repair. Therefore, it is essential in any decellularisation process that the histo-architecture and biomechanical properties of these complex tissues are preserved.

The composition of bone matrix is approximately one third organic and two thirds inorganic matter. The organic matter, synthesized by the osteoblasts is collagen and proteins like proteoglycans and glycoproteins. Other cells present in bone are osteocytes, osteoclastsosteoprogenitors and bone lining cells. The other inorganic matter is mostly crystallized calcium phosphate salts and calcium carbonate, and a few other minerals. Bone matrix is a composite which means it has characteristics of the hard, strong inorganic matter and some flexibility and give from the collagen.

A major problem associated with any implants comprising a composite or mixture of different natural biological materials, each having different properties and functions, is that one particular decellularisation treatment may be effective for one tissue type of the composite/mixture but may be deleterious to another tissue type resulting in an impaired overall composite product that is not fit for purpose. The problem is compounded according to the number of different tissue types in the composite implant. For example, since bone itself is a composite material any implant that comprises bone plus another tissue type, for example ligament, meniscus and/or enthesis (a cartilage-like tissue found where the meniscus or ligament attaches to the bone) is effectively three or more different tissue types each requiring specific decellularisation treatments that do not impair or alter the characteristics of any of the other tissue types.

Osteochondral lesions can cause pain and a lack of motion in joints but also often result in increased cartilage wear and degradation of the synovial joint to an osteoarthritic state. A number of surgical interventions can be employed to repair initial cartilage damage and prevent disease progression to osteoarthritis. These treatments, however are often ineffective, providing a mechanically inferior repair material, lack integration with surrounding host tissues or have issues associated with donor site morbidity. Tissue engineered scaffolds made from synthetic or natural materials are in development and avoid donor site morbidity issues, but often still do not provide the same mechanical function as natural cartilage. A natural, xenogenic, acellular composite osteochondral graft with the same composition and structure should have the same biomechanical function as natural cartilage. By removing the cells such grafts should be biocompatible. By retaining the subchondral bone, composite grafts should integrate well with the surrounding host tissues. No donor site is required and grafts should eventually be regenerated by host cells.

A natural decellularised composite bone-connective tissue-bone replacement or osteochondral tissue matrix that is immunologically inert and essentially devoid of any cells would offer immediate benefit to patients and the medical profession alike.

In particular, an "off the shelf" meniscal and bone replacement would address the social and economic needs of the ageing population with meniscal injuries enabling high levels of activity, capacity to work and quality of life. Similarly, a ligament replacement, osteochondral or repair implant would also be of significant value to sufferers of acute and chronic ligament and bone injuries alike. In particular a bone-patella tendon-bone implant would be of immense benefit to sufferers of anterior cruciate ligament injuries of the knee joint.

BRIEF SUMMARY OF THE DISCLOSURE

According to a first aspect of the invention there is provided a product comprising a decellularised natural multi-composite bone transplant material characterised by the absence (100%) or substantial absence (90%) of cells in the whole multi-composite product.

Reference herein to a "multi-composite bone transplant material" is a transplant material that is made up of bone and at least one other distinct biological tissue such as a connective tissue or cartilage and includes a bone-connective tissue-bone composite or an osteochondral composite.

Preferably, the decellularised bone-connective tissue-bone product retains its original histoarchitecture, structural collagen composition and biomechanical properties as compared to a native fresh cellularised counterpart composite tissue. The products of the present invention have been histologically, structurally and immunohistologically characterised to be of comparable equivalence of natural/native tissue. Results have shown that the decellularised products of the invention also retain collagen and that it is not denatured during the decellularisation methods of the present invention, moreover immunohistochemical evaluation showed retention of major extra cellular matrix (ECM) components but loss of glycosaminoglycans (GAGs), collagen IV and collagen VI.

Preferably, the decellularised bone multi-composite product may be characterised by a total genomic DNA (gDNA) content of all tissue in the multi-composite product of between 0 to 10% of the native tissue, more preferably by a gDNA content of 0 to 7.5% of the native tissue and more preferably still be a gDNA content of 0 to 5%. Results have shown that for example that isolated meniscal tissue can be processed to within 2.5 to 5.0% of a gDNA content as compared to native meniscal tissue, whereas for isolated bone tissue this is around 5 to 10% as compared to native tissue.

Preferably, the decellularised product is immunologically inert.

Preferably, the decellularised multi-composite bone transplant product is derived from allogeneic or xenogeneic tissue. Preferably, the xenogeneic tissue is porcine.

Preferably the connective tissue is selected from the group comprising ligaments and meniscus.

Preferably the meniscus is medial meniscus tissue. The bone-medial meniscus-bone product includes attachment tissue or enthesis at either end of the meniscus attaching the meniscus to each terminal bone block (FIG. 8B). The bone-medial meniscus-bone product of the present invention thus includes enthesis tissue and is thus a multi-composite material.

In the instance of the connective tissue comprises a ligament, the ligament is selected from the group comprising head and neck ligaments, wrist and finger ligaments, knee ligaments, thorax ligaments, foot ligaments and pelvis ligaments.

Head and neck ligaments may be selected from the group comprising cricothyroid ligament, periodontal ligament and suspensory ligament of the lens. Wrist ligaments may be selected from the group comprising palmar radiocarpal ligament, dorsal radiocarpal ligament, ulnar collateral ligament and radial collateral ligament. The thorax ligament may be the suspensory ligamants of the breast. Knee ligaments may be selected from the group comprising anterior cruciate ligament (ACL), lateral collateral ligament (LCL), posterior cruciate ligament (PCL), medial collateral ligament (MCL), cranial cruciate ligament (CRCL)—quadruped equivalent of ACL, caudal cruciate ligament (CACL)—quadruped equivalent of PCL and patellar ligament. Pelvic ligaments may be selected from the group comprising anterior sacroiliac ligament, posterior sacroiliac ligament, sacrotuberous ligament, sacrospinous ligament, inferior pubic ligament, superior pubic ligament and suspensory ligament of the penis.

Preferably the ligament is a knee ligament and more particularly is a patella tendon. As with the bone-medial meniscus-bone product, the bone-tendon-bone product will also include enthesis tissue and again is thus a multi-composite material.

According to a further aspect of the invention there is provided a method of preparing a decellularised donor bone multi-composite tissue matrix for subsequent implantation into a host comprising the steps of:
  (i) freezing and thawing the multi-composite tissue matrix;
  (ii) subjecting bone blocks to a fluid jet;
  (iii) ultrasonicating the composite tissue matrix;
  (iv) in the instance of the multi-composite tissue matrix comprises a bone-connective tissue—bone structure, teasing apart fascicles at an enthesis region;
  (v) incubating the multi-composite tissue matrix in a hypotonic buffer;
  (vi) incubating the multi-composite tissue matrix in a hypotonic solution comprising an anionic detergent;
  (vii) incubating the multi-composite tissue in a solution comprising at least one nuclease enzyme;
  (viii) washing the multi-composite tissue matrix;
  (ix) incubating the multi-composite tissue matrix with an oxidising agent and;
  (x) further washing of the multi-composite tissue matrix.

The freeze/thaw process preferably comprises freezing the composite tissue matrix at, for example between −10 to −85° C., typically at −20° C. for bone-meniscus-bone tissue and at −85° C. for bone-patella tendon-bone tissue. This is conducted at first on phosphate buffered saline (PBS) moistened material and then thawing the composites to around room temperature.

Bone block(s) of the composite tissue matrix is/are then subjected to pressurised fluid jets (step ii), the fluid being either water or phosphate buffered saline (PBS). This process is referred to as "water pik" and is used to remove bone marrow and blood cells especially from cancellous bone blocks. Typically, between 250-600 ml of fluid is used to water pik each bone block Preferably, the ultrasonic (US) power is applied via a sonicating bath to a solution in which the multi-composite tissue matrix is immersed. Typically the solution surrounding the multi-composite tissue matrix is a buffered solution such as phosphate buffered saline.

In step (iv) in the instance of the multi-composite tissue matrix comprises a bone-connective tissue—bone structure the fascicles in the enthesis region are teased apart using a scalpel and without severing any of the fibres creating space between the fascicles to improve subsequent diffusion of wash solutions In step (v) incubating the multi-composite tissue matrix in a hypotonic solution comprises a first freeze thaw incubation. Freezing is maintained for between 2-24 hours and subsequently defrosting the tissue for about 2, 3 or 4 hours until it reaches room temperature or in the case of bone-meniscus-bone thawing is at 40-45° C. This process is carried out at least once and preferably twice or three times in the absence of a hypotonic buffer and repeated again at least once and preferably twice when the tissue is immersed in the hypotonic buffer. The hypotonic buffer comprises 10 mM Tris solution at mildly alkaline conditions (pH 8.0 to 8.2 for example) including 10 KIU/ml aprotonin. It will be appreciated that the freeze/thaw in the presence and absence of a hypotonic buffer may be reversed and optionally alternated. Following the freeze/thaw conditions the composite tissue matrix is then incubated in the hypotonic wash solution at around at 40-45° C.

A hypotonic solution is one in which the concentration of electrolyte is below that in cells. In this situation osmotic pressure leads to the migration of water into the cells, in an attempt to equalize the electrolyte concentration inside and outside the cell walls.

In step (vi) the multi-composite tissue matrix is incubated with an anionic detergent such as sodium dodecyl sulphate (SDS). Preferably this is present in the hypotonic wash solution at a concentration in the range of 0.03-0.3% (v/v) and more preferably still is present at approximately 0.10 to 0.15% (v/v). Following incubation with SDS the composite tissue matrix is washed in PBS including 10 KIU/ml aprotonin at pH 7.2-7.4 for multiple cycles (4-8) over 6-72 hours.

In step (vii) the multi-composite tissue matrix is then incubated with nuclease enzymes to digest any remaining nucleic matter which has been shown to act as sites for calcification.

A typical but non-limiting nuclease incubating solution 50 mM Tris solution pH7.5-7.7, 10 mM $MgCl_2$, bovine serum albumin (50 μg/ml) with RNase (1 U·$ml^{-1}$) and DNase (50 U/ml).

Tissue is preferably incubated for about 2, 3 or 4 hours typically at about 37° C. with the nuclease solution whilst being gently agitated. This is repeated, preferably for three cycles.

Following incubation with the nuclease solution, the tissue is preferably then further incubated for about 12-48 hours and typically 24 hours in a hypertonic solution comprising Tris in solution (0.05 M) at pH 7.5-7.7 plus 1.5 M NaCl at around 40-45° C. or a temperature below that which may cause denaturation of the collagen proteins. Followed by a PBS wash as described above.

In step (ix) the composite tissue matrix is incubated with an oxidizing agent, preferably the oxidising agent is peroxyacetic acid ($C_2H_4O_3$) also known as peracetic acid and commonly abbreviated to PAA.

Preferably, the concentration of PAA is in the range of 0.01-0.5% v/v and more preferably still is about 0.1% PAA (v/v).

The final steps (x) of preparing the decellularised bone-connective tissue-bone composites comprise extended washes in PBS (as described above).

The method may also further include a step of optionally incubating the composite tissue matrix with an oxidising agent and;

A further option step to the methods of the invention includes preparation for storage at between −10 to −85° C., typically at −20° C. for bone-meniscus-bone tissue and at −85° C. for bone-patella tendon-bone tissue. Storage is typically on PBS moistened material. Bone-patella tendon-bone composites may also be stored at 4° C.

It will be appreciated throughout the description of the methods of the present invention that the timings, temperatures and concentrations recited are given as examples only and are not intended to limit the scope of the invention.

According to a further aspect of the invention there is provided a transplant product produced by the methods of the present invention.

According to a yet further aspect of the invention there is provided a decellularised natural multi-composite bone-connective tissue-bone or osteochondral transplant material obtainable by the method of the present invention for use as an implant.

According to a yet further aspect of the invention there is provided use of a decellularised natural multi-composite bone-connective tissue-bone or osteochondral transplant material obtainable by the method of the present invention as a transplant tissue.

According to a yet further aspect of the invention there is provided a method of treatment of an individual requiring meniscal repair or replacement surgery comprising the steps of preparing a decellularised natural donor bone-medial meniscal-bone transplant product according to the methods of the invention and replacing the defective or damaged meniscus with the decellularised natural bone-medial meniscus-bone transplant product.

According to a yet further aspect of the invention there is provided a method of treatment of an individual requiring anterior cruciate ligament knee repair or replacement surgery comprising the steps of preparing a decellularised natural donor bone-patella tendon-bone transplant product according to the methods of the invention and replacing the defective or damaged area with the decellularised natural bone-patella tendon-bone transplant product.

According to a yet further aspect of the invention there is provided a method of treatment of an individual requiring osteochondral repair or replacement surgery comprising the steps of preparing a decellularised natural osteochondral product according to the methods of the invention and replacing the defective or damaged osteochondral tissue with the decellularised natural osteochrondral transplant product.

It will be appreciated that any feature ascribed to an aspect of the invention is equally applicable to each and every other aspect of the invention mutatis mutandis.

BRIEF DESCRIPTION OF THE DRAWINGS

Embodiments of the invention are further described hereinafter with reference to the accompanying drawings, in which:

FIG. 5 shows a series of biochemical assays performed on fresh and decellularised meniscus and bone sections.

FIG. 11A shows the SDS concentration μg/mg during the process and FIG. 11B shows the SDS concentration μg/mg in the outer, inner meniscus, attachment region, bone and entire scaffold.

FIG. 29 shows control bone plug inserted into ovine condyle and scanned by micro-CT FIG. 30 shows decellularised bone plug inserted into ovine condyle and scanned by micro-CT FIG. 31 shows mean trabecular thickness and spacing of control porcine pins and ovine condyles.

DETAILED DESCRIPTION

Figure 1:
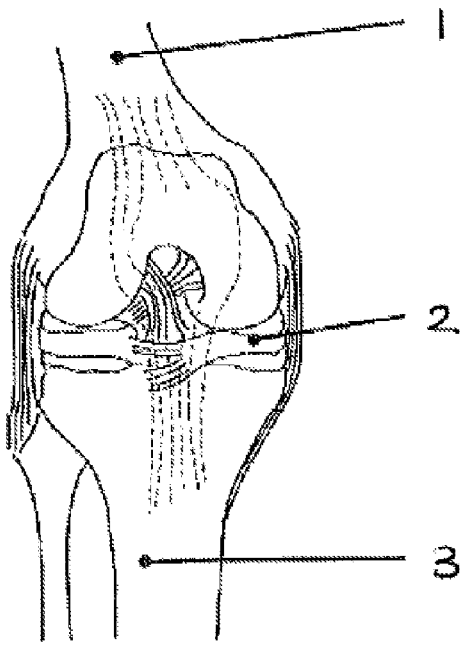
FIG. 1 shows a representation of knee joint.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Reference herein to a "native" or "natural" implant or scaffold or tissue matrix is intended to include allograft or xenogeneic derived biological tissues. The terms "implant product" or "transplant product" or "scaffold" or "matrix" are interchangeable and refer to the biological material prepared by the decellularisation methods of the present invention.

Reference herein to a composite implant is intended to include an implant comprising different natural biological materials/tissues each having different properties and functions.

Bone itself is a composite material having characteristics of the hard, strong inorganic matter and some flexibility and give from the organic collagen matter and in combination with connective tissue the products of the invention are a multi-composite transplant products.

Reference herein to "decellularised" is intended to include biological material that has undergone methodology to remove cells so that the final product is substantially acellular that is to say it is devoid of cells be they viable of non-viable cells. The terms "decellularised" and "acellular" are interchangeable. By substantially decellularised or acellular this includes between 90% and up to 100% removal of all living or viable cells from all parts of the multi-composite transplant product, the products of the present invention are therefore practically devoid of cells such as for example fibrochondrocytes and fibroblasts and have a negligible, if any, gDNA content and as such they are most appropriate materials for subsequent transplantation.

It should be noted that although WO 2008/059244 describes a method of decellularising meniscal soft tissue, it was found not to be a satisfactory method for decellularising a bone-connective tissue-bone composite implant. Indeed results showed whole cells in the enthesis region and softening of the bone attachments.

Preparation of Bone-Connective Tissue—Bone Tissue

FIG. 1 shows a schematic representation of a knee joint, the femur (1) being separated from the tibia (3) by the medial meniscus (2). The meniscus is a fibrocartilage structure with a highly organised extracellular matrix. The meniscal attachment site on the tibial plateau comprises layers of cartilage, enthesis and bone held together by ligaments. Bone-medial meniscus-bone (BMB) and bone-patella tendon-bone (BPTB) were dissected from six month old pigs within 24 h of animal slaughter.

BMB were obtained by sharp dissection, initially separating the meniscus from the surrounding connective tissue and perimeniscal capillary plexus followed by sawing through the tibial plateau to obtain bone blocks at either end approximately 10 mm×10 mm×15 mm. Once removed from the knee, any remaining connective tissue was removed using blunt dissection and washed in PBS (Oxoid) to remove excess blood. Samples were then stored at −20° C. on PBS moistened filter paper for future use.

In a similar manner, porcine BPTB were obtained by sharp dissection, initially separating the patella tendon from the surrounding connective tissue and fat pad followed by releasing the patella, and sawing through the tibia to release the tibial attachment plus bone. Once removed from the knee, any remaining connective tissue and fat was removed by blunt dissection. The tibial bone block and patella bone were then trimmed and shaped to provide bone plugs circa 2 cm wide by 3 cm in length. They were then washed in PBS to remove excess blood and stored at −80° C. on PBS moistened filter paper.

Pin Harvest

Osteochondral pins (9 mm diameter, 10 mm deep) were extracted from the medial condyle of porcine knees and the medial femoral groove of bovine knees. Pins were stored frozen at −20° C. until required.

Tissue/Histology Preparation

Tissue specimens were fixed in 10% (v/v) neutral buffered formalin for 48 h and then dehydrated and embedded in paraffin wax. Serial sections of 6 µm in thickness were taken with 1 in 10 sections used. Standard haematoxylin and eosin (H&E) (Bios Europe Ltd, Skelmersdale, UK) staining was used to evaluate tissue histioarchitecture.

Immunohistochemistry Specimen Preparation

Tissue specimens were fixed in zinc fixative for 16 hours and then dehydrated and embedded in paraffin wax. Bone sections were fixed in zinc fixative for 16 hours and then decalcified using 12.5% (w/v) EDTA solution, prior to dehydration and embedding in paraffin. Serial sections of 6 µm in thickness were taken with 1 in 10 sections used. Sections were then dewaxed using xylene and rehydrated in a graded ethanol series. Antigen retrieval was carried out using proteinase K (20 µg/mL, Dako) at room temperature for 20 mins. Peroxidase activity was blocked by immersing sections in 3% (v/v) hydrogen peroxide in distilled water at room temperature for 10 mins. Endogenous enzyme activity was blocked using the blocking agent included in the Ultra Vision One detection system (Thermo Fisher Scientific).

Sections were incubated with the following antibodies for 1 hour at room temperature: Anti-collagen I (MAB3391, Millipore, 1:100), anti-collagen II (MAB1330, Millipore, 1:50), anti-collagen III (ab7778, Abcam, 1:100), anti-collagen IV (M 0785, Dako, 1:50), anti-collagen VI (MAB3303, Millipore, 1:50), anti-osteocalcin (0400-0040, AbD Serotec, 1:100), and anti-alpha-gal (ALX-801-090, Enzo Life Sciences, 1:3). Antibodies were visualised using the kit-provided (UltraVision One Detection System, Thermo Fisher Scientific) polymer-horse radish peroxidase complex utilising 3,3'-diaminobenzidine (DAB) as a substrate to develop a brown colour.

Hydroxyproline Assay.

Prior to performing the hydroxyproline assay, samples were lyophilized to a constant weight before being hydrolysed by incubation with 6M hydrochloric acid (HCL) for 4 h at 120° C. and neutralized using sodium hydroxide (NaOH). The procedure adopted was based on the method described by Edwards and O'Brien. Standard calibrator solutions were made up using trans-4-hydroxy-L-proline (Sigma). Test solution (50 µl) was added to wells of a flat bottomed 96-well plate to which 100 µl of oxidizing solution (chloramine T hydrate; Sigma) was added and left for 5 min with gentle agitation. Ehrlich's reagent (100 µl) was then added to each well. The plate was then covered and incubated at 60° C. in a water bath for 45 min prior to the absorbance being read at 570 nm. The concentration of hydroxyproline was then determined by interpolation from a hydroxyproline standard curve.

Assay for Denatured Collagen Following Alpha Chymotrypsin Treatment

Samples of the tissues were incubated with α-chymotrypsin (5 mg/mL, Sigma-Aldrich) at 30° C. for 24 hours to digest denatured collagen. Digests were then centrifuged at 600 g for ten minutes and hydroxyproline assays (as above) were carried out on the supernatant.

Sulphated Sugar Assay.

Prior to performing the sulphated sugar assay, samples (n=3) were lyophilized to a constant weight before enzymatically digesting the tissue in papain buffer (1 mg·ml$^{-1}$ papain, Sigma, in PBS at pH 6.0 with 5 mM cysteine-HCl, Sigma, and 5 mM Na$_2$EDTA, VWR) for 48 h at 60° C. The method was adapted from Farndale et al. [30]. Briefly, standard calibrator solutions were made up using chondroitin sulphate (Sigma). Standard or test solution (40 µl) were added to 250 µl of 1,9-dimethylene blue solution in wells of flat bottomed 96-well plates. The absorbance was then read at 525 nm after 1 min. The resultant concentration of sulphated sugars, representative of glycosaminoglycans (GAG) was then determined by interpolation from the standard curve.

Extraction and Analysis of gDNA Presence

Genomic DNA (gDNA) was extracted using a DNA isolation kit for tissues (Qiagen). Briefly, 25 mg of fresh and 100 mg of decellularized porcine meniscal tissue was digested using a Proteinase K solution (n=3). Following this, digests of meniscal tissue were processed by centrifuging through kit provided mini-spin columns to capture and elute DNA. Fresh and decellularised bone was digested using a proteinase K solution also containing 12.5% (w/v) EDTA and 1% SDS at 56° C. overnight. Samples were then processed as for meniscal tissue. DNA was quantitated by measuring absorbance at 260-280 nm in a Nanodrop spectrophotometer (Labtech Int, Ringmer, UK).

Qualitatively the presence of functional DNA was analysed by amplification of glyceraldehyde 3-phosphate dehydrogenase (GAPDH), collagen I and β-actin genes using PCR. Samples were prepared for PCR by mixing 25 µL of master mix (Fermentas Life Sciences, UK) with 22 µL of nuclease-free water, 1 µL each of forward and backward primers (Sigma), and 1 µL of sample DNA extracted as described above. Samples were mixed and placed in a PCR machine and once the program was complete amplified genes were visualised using an E-gel PowerBase system (Invitrogen, Paisley, UK). A dry 4% (w/v) agarose E-gel (Invitrogen) was inserted into the base prior to the addition of samples. Resuspended samples (13.5 µl) were prepared by adding loading buffer (1.5 µl, Invitrogen) to allow ease of sample loading. The total volume was then loaded into individual lanes of the E-gel and then electophoresed. A 1 kb DNA ladder (Fermentas Life Sciences, UK) was run in parallel to estimate the size of the DNA isolated. Staining with SYBR SAFE (Invitrogen) allowed visual inspection on a Kodak Gel Logic 1500 system (Eastman Kodak Company, Harrow, UK).

Bone Sample Preparation

Bone samples were fixed in 10% (v/v) NBF and dehydrated using a graded ethanol series up to 100% ethanol. Samples were then infiltrated using Technovit 7200 VLC resin (Exact) in a graded resin/ethanol series up to 100% resin and embedded in resin blocks for sectioning using a bone saw (Exact). Sections were obtained by cutting 400 µm slices from the blocks using a bone saw and grinding down to a final thickness of 20 µm.

Modified McNeal's Tetrachrome Stain

Resin embedded sections were immersed in 50% (v/v) ethanol for ten minutes, rinsed in distilled water and then immersed in 0.1% (v/v) formic acid for ten minutes to expose the section. Slides were then washed three times using distilled water and immersed in modified McNeal's Tetrachrome (0.1% (w/v) methylene blue chloride, 0.16% (w/v) azure A eosinate, 0.02% (w/v) methyl violet, 0.05% (w/v) toluidine blue) for five minutes. Sections were then rinsed in distilled water and immersed in 0.1% (w/v) basic fuchsin for 30 seconds followed by a final rinse in distilled water.

Differential Scanning Calorimetry

Samples (n=3) of native and decellularised BMB (~10 mg) were taken from inner, outer, attachment, enthesis and bone regions and dehydrated in a graded ethanol series (0, 20, 40, 60, 80, and 100%). Samples were then dried at room temperature under vacuum for 30 mins to remove ethanol and heated at 10° C./min up to 200° C. to obtain thermal transition temperatures.

Indentation Testing

Cylindrical samples of 7 mm diameter (n=5) were taken from the central region of native and decellularised meniscus. A 1 mm thick slice was taken from the centre of the cylinder, loaded using a 2 mm flat indenter on the end of an aluminium shaft (23 g) of a lab-built indentation rig, and the displacement measured over an hour using a linear variable differential transformer (LVDT). Linear regression was performed on LVDT measurements to convert voltage to displacement.

The composite connective tissue and bone replacements of the present invention would be regulated as a Class III medical device, thus advantageously providing a low cost regenerative solution with no change to current surgical practices, and the benefit of reduced time to patient benefit compared to other regenerative medicine approaches.

Example 1

Figure 2:
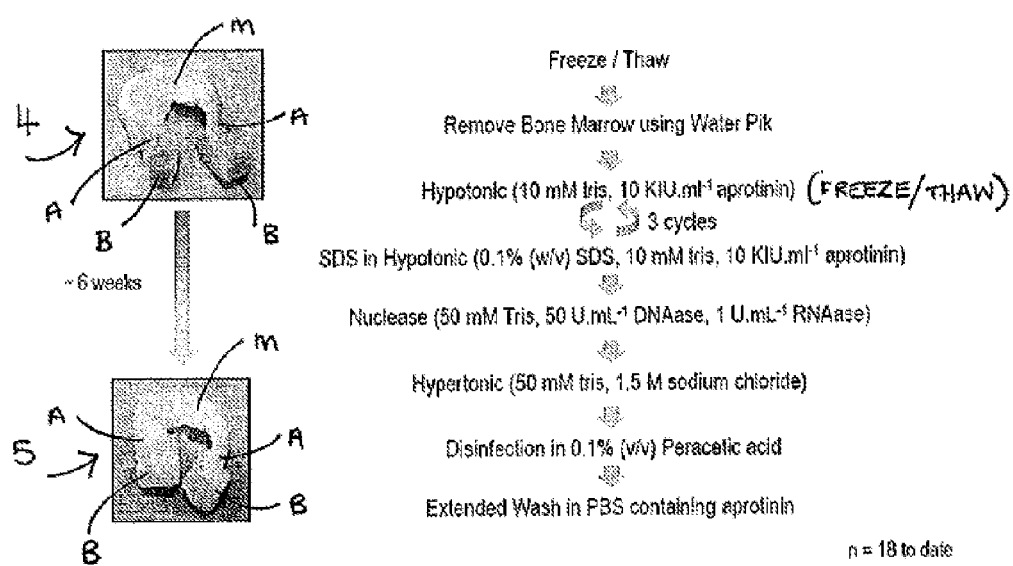
FIG. 2 shows a typical decellularisation process for a bone-medial meniscus-bone implant.

FIG. 2 shows a typical decellularisation process for a bone-connective tissue-bone implant, in this instance the sample is a bone-medial meniscus-bone (BMB) implant. The process can take up to six weeks to complete from a fresh sample (4) to a decellularised sample (5). The transplant material comprises at either end bone portions (B) each bone portion being attached to an attachment region (A) interconnected by a meniscus (M). Bone-medial meniscus-bone was dissected from six month old pigs before it was subjected to a decellularisation process. The BMB sample was subjected to a freeze at −20° C. on PBS moistened paper for about 3 hours and then thawed at 40-45° C. for 1 hour for three cycles. The bone blocks were then cleaned with a water pik ejecting either water or PBS under pressure at room temperature using about 300 ml of fluid per bone block. Fresh bone comprises blood and bone marrow cells and it is desirous that these be flushed out of the bone plugs. The fascicles in the enthesis region were then teased apart without severing any of the fibres using a scalpel after which samples were subjected to a further freeze/thaw in hypotonic solution comprising 10 Mm TRIS solution at approximately pH 8.0 including about 10 KIU/ml of aprotinin. Freezing was conducted at −20° C. for about 3 hours and thawing at 40-45° C. for about 1 hour in three cycles. Samples were then washed in hypotonic 10 mM TRIS buffer plus aprotinin at 40-45° C. followed by washing in hypotonic buffer plus aprotinin with 0.1% (w/v) SDS at 40-45° C. The hypotonic buffer/hypotonic buffer plus SDS washes were repeated twice. Following this, samples were washed in PBS at pH 7.2-7.4 with aprotinin for 72 hours in six 12-hour washes and then subjected to a nuclease treatment comprising 50 mM TRIS, 10 mM $MgCl_2$ and RNase and DNase at 1 and 50 U·ml respectively at pH 7.5-7.7 at 37±1° C., 80 rpm for 3 hours for three cycles. A further PBS wash was performed at pH 7.2-7.4 containing 10 KIU/ml aprotinin at 4° C., 320 rpm for 12-16 hours in a single cycle followed by a hypertonic solution 50 mM TRIS, 1.5 M NaCl at 7.5-7.7 pH for 24 hours at 40-45° C. This was then followed by a further PBS wash and disinfection by, for example, a peracetic acid treatment (0.1% v/v at 27° C., 320 rpm for 3 hours). Finally, further extended PBS end washes are performed at 160 rpm, samples may then be frozen on PBS moistened paper at about −20° C. for storage.

The protocol for BPTB was similar to that described for BMB. The BPTB was thawed at room temperature. The bone blocks were then cleaned with a water pik ejecting either water or PBS under pressure at room temperature using about 300 ml of fluid per bone block. The BPTB were refrozen in hypotonic buffer for 16 h and thawed. This was repeated. Once thawed at room temperature, the fascicles in the enthesis region were then teased apart without severing any of the fibres using a scalpel after which the BPTB was incubated in hypotonic buffer with aprotinin at 40-45° C. for 23-25 hours. The BPTB were then incubated in hypotonic buffer containing 0.1% (v/v) SDS and aprotinin for 23-25 hours at 40-45° C. This process was repeated. Following this, samples were washed in PBS at pH 7.2-7.4 with aprotinin and then subjected to a nuclease treatment comprising 50 mM TRIS, 10 mM $MgCl_2$ and RNase and DNase at 1 and 50 U·ml respectively at pH 7.5-7.7 at 37±1° C., 80 rpm for 3 hours for three cycles. A further PBS wash was performed at pH 7.2-7.4 containing 10 KIU/ml aprotinin at 4° C. at 320 rpm for 12-16 hours in a single cycle followed by a hypertonic solution 50 mM TRIS, 1.5 M NaCl at 7.5-7.7 pH for 24 hours at 40-45° C. This was then followed by a further PBS wash and disinfection by, for example, a peracetic acid treatment (0.1% v/v at 27° C., 320 rpm for 3 hours). Finally, further extended PBS end washes are performed at 160 rpm, samples may then be frozen on PBS moistened paper at about −80° C. for storage.

Example 2

Figure 3:
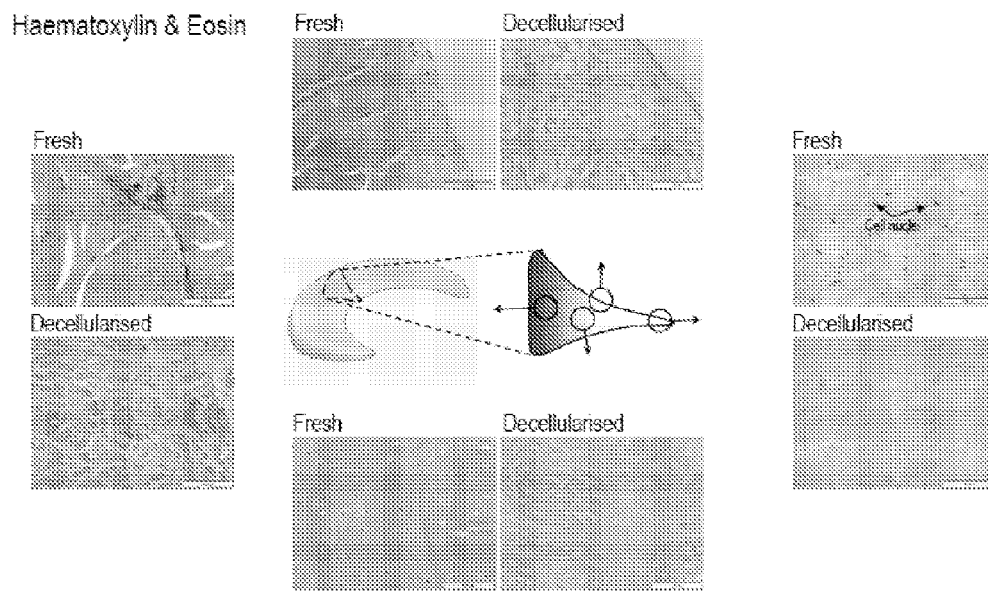
FIG. 3 shows haematoxylin and eosin histochemical staining for different sections of fresh and decellularised meniscus.

Histochemical staining of formalin fixed paraffin-embedded meniscus (M) by haematoxylin (which stain cell nuclei blue/black) and eosin (which stains cytoplasm and connective tissue pink) shows that the decellularisation method of the present invention is able to remove cells from both inner and outer portions of meniscal tissue (FIG. 3).

Figure 4:
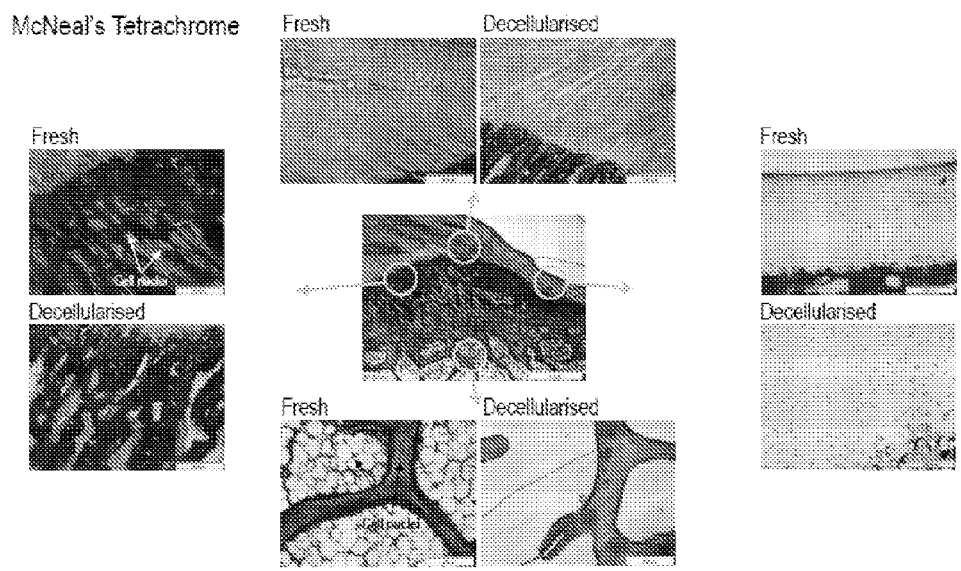
FIG. 4 shows modified McNeal's tetrachrome histochemical staining of different sections of formalin fixed resin-embedded bone of fresh and decellularised attachment samples.

Similarly, using modified McNeal's tetrachrome histochemical staining of formalin fixed resin-embedded bone (B) was conducted. McNeal's Tetrachrome uses: toludine blue to stain for cartilage (blue/purple); eosin to stain cytoplasm and connective tissue (pink); methylene blue which stains DNA (blue) and; basic fuchsin which stains bone (red/purple). Results showed that using the methods of the present invention the attachment site and bone tissue was decellularised as compared to fresh tissue (FIG. 4).

Example 3

Figure 5A:
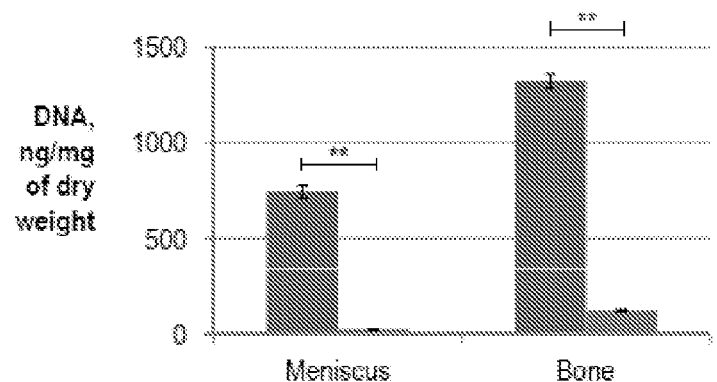
FIG. 5A shows the DNA ng/mg of dry weight.

A series of biochemical assays were performed on fresh (left hand side of each bar) and decellularised (right hand side of each bar) meniscus, attachment and bone tissue prepared according to the methods of the present invention. FIG. 5A shows the DNA ng/mg content of dry weight of both fresh and decellularised meniscus and bone, for the decellularised samples there was a highly significant ($p<0.01$) reduction in DNA content. This result taken in conjunction with the DNA analysis by PCR of 'housekeeping' genes associated with functionality of meniscus and bone (GAPDH, β actin and collagen I) where an absence of functional DNA was observed in decellularised scaffolds indicates that using the methods of the present invention the BMBs of the present invention are effectively completely decellularised.

Example 4

Figure 5B:
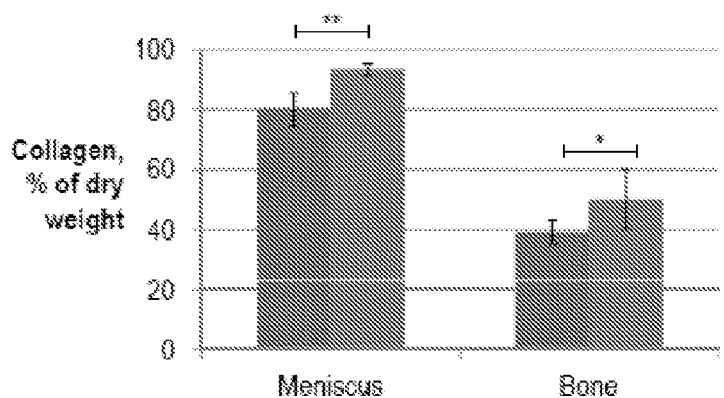
FIG. 5B shows the percentage of collagen dry weight.
Figure 5C:
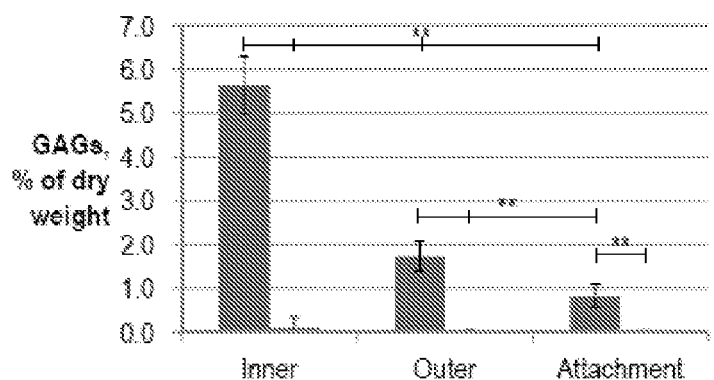
FIG. 5C shows the percentage of glycosaminoglycans (GAGs) of dry weight and FIG. 5D shows the percentage of calcium of dry weight.

Biochemical assays for the percentage of dry weight of collagen (FIG. 5B), glycosaminoglycans (FIG. 5C) and calcium (FIG. 5D) of fresh and decellularised tissue showed that, for collagen, there was a significant ($p<0.05$) increase in collagen in decellularised meniscus and a less significant ($p<0.05$) increase in collagen in decellularised bone. The increase in percentage collagen content of decellularised material is probably due to removal of other material.

Figure 5D:
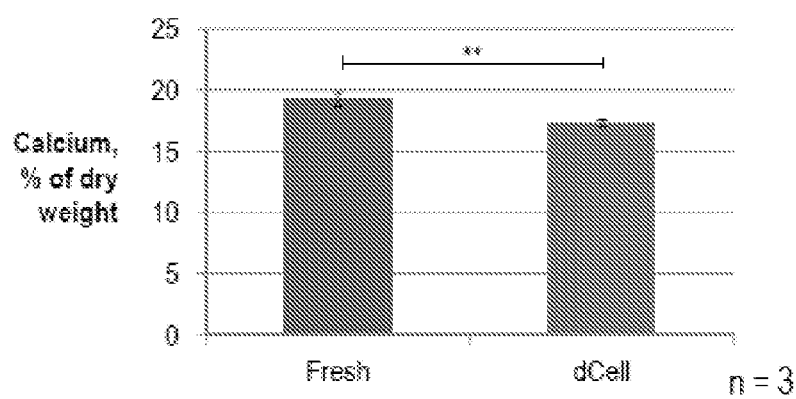
Figure 6:
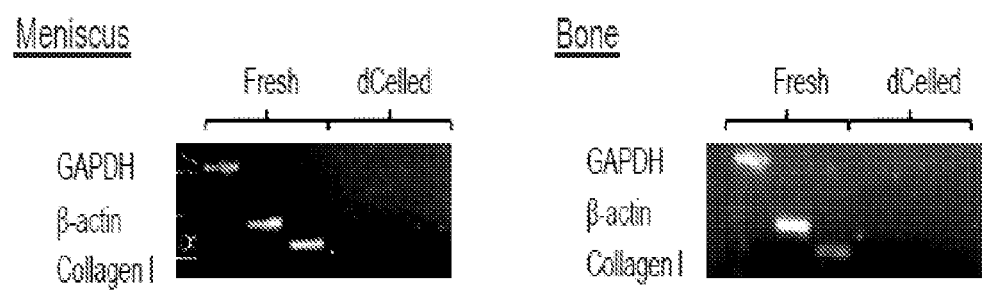
FIG. 6 shows DNA analysis of GAPDH, β-actin and collagen I of fresh and decellularised meniscus and bone.

The percentage dry weight of glycosaminoglycans in inner and outer areas of the meniscus and the attachment tissue showed that in all instances there was a highly significant ($p<0.01$) decrease in decellularised tissue as compared to fresh tissue. In addition it was observed that there is a higher concentration of glycosaminoglycans in the cartilage-like region of the meniscus. However, results show that the methods of the present invention are effective at removing glycosaminoglycans from all areas of the tissue samples. There was a small but significant decrease in the percentage of calcium of dry weight (FIG. 5D).

Example 5

Figures 7, 8A:
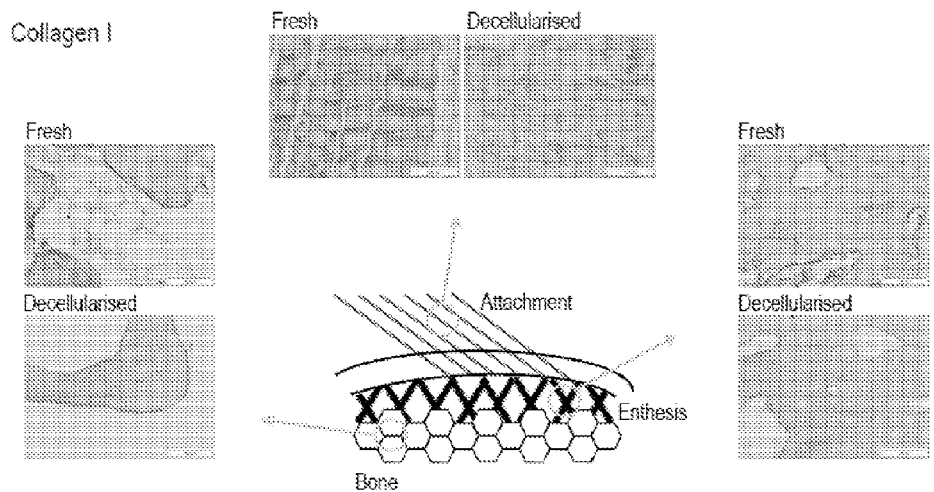
FIG. 7 shows immunohistochemical staining for collagen I for the attachment site, enthesis and bone of fresh and decellularised samples.
FIG. 8A shows a tabulated summary of a variety of extra-cellular matrix components (collagen I, collagen II, collagen III, collagen IV, collagen VI and osteocalcin) for fresh and decellularised inner and outer meniscus, attachment and bone areas of a bone-medial meniscus-bone transplant.
Figure 8B:
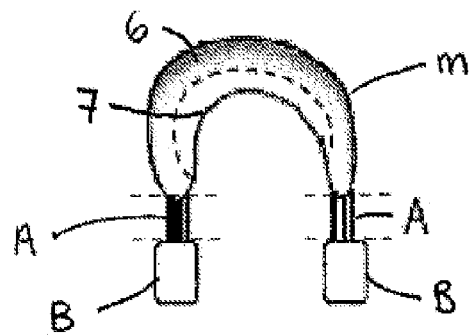
FIG. 8B shows the regions of the bone-medial meniscus-bone implant from which samples were taken for histochemical staining.

A study was conducted on the immunohistochemistry of the attachment site (FIG. 7). Sections of the attachment, enthesis and bone areas were stained using antibodies in order to detect collagen I. FIG. 8B shows a summary table of immunohistochemical staining of sections of inner (7), outer (6) meniscal (M), attachment (A) and bone (B) of both fresh and decellularised material (FIG. 8A). The extracellular matrix (ECM) components assessed were collagen I, collagen II, collagen III, collagen IV, collagen VI and osteocalcin and scored (+++) as very strong, (++) strong, (+) positive, (+/−) less positive and (−) negative. Results showed that for collagen I, collagen II and osteocalcin there was no difference in scores for all tissue section in either fresh or decellularised samples. There was a slight decrease in collagen III in decellularised attachment tissue compared to fresh tissue, all other tissues showed parity of staining strength.

There was also a reduction in collagen VI in inner (7), outer meniscal (6) tissue and attachment tissue (A) of decellularised material as compared to fresh material. There was no difference in collagen VI between fresh and decellularised bone. Collagen VI however was reduced in decellularised inner, outer meniscus and attachment tissue as compared to fresh tissue, no discernible difference was observed in fresh or treated bone for collagen VI. Decellularised tissue (all types) showed an absence of collagen IV as compared to fresh tissue. This data indicates that apart from collagen IV decellularised inner, outer meniscus attachment and bone have the same or similar collagen and osteocalcin content as compared to counterparts of fresh tissue.

Example 6

Figure 9:
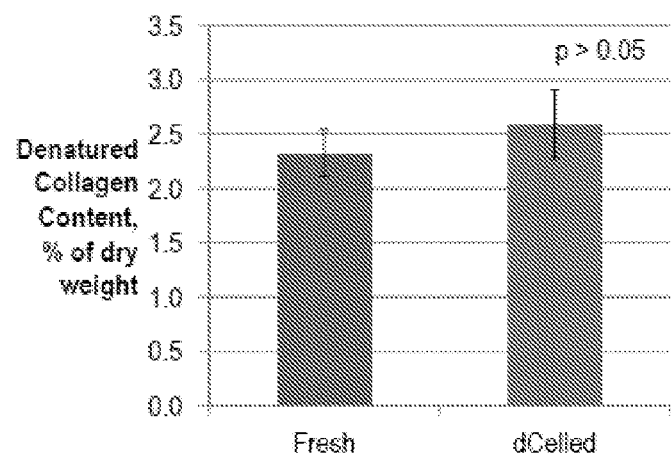
FIG. 9 shows percentage denatured collagen content of dry weight following α-chymotrypsin digestion followed by hydroxyproline assay for fresh and decellularised scaffolds.
Figure 10:
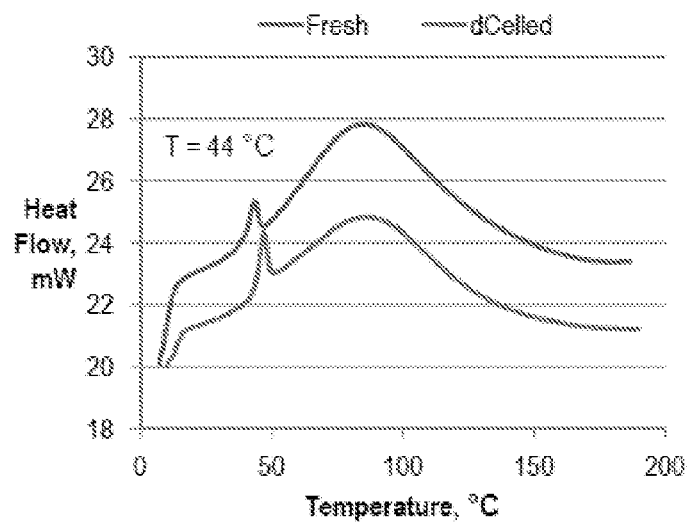
FIG. 10 shows collagen denaturation of fresh and decellularised fresh and decellularised scaffolds as assessed using differential scanning calorimetry.

Studies were conducted to assess the extent of collagen denaturation during the decellularisation process of the present invention. Fresh and decellularised meniscus were assessed for percentage denatured collagen content of dry weight following α-chymotrypsin digestion followed by hydroxyproline assay. Results showed that denatured collagen was significantly higher (p>0.05) in treated tissue as compared to fresh tissue (FIG. 9). A further assay using differential scanning calorimetry as a measurement of heat capacity for both fresh and decellularised meniscus material (FIG. 10) confirmed that collagen was not denatured in a decellularised scaffold.

Example 7

Figure 11A:
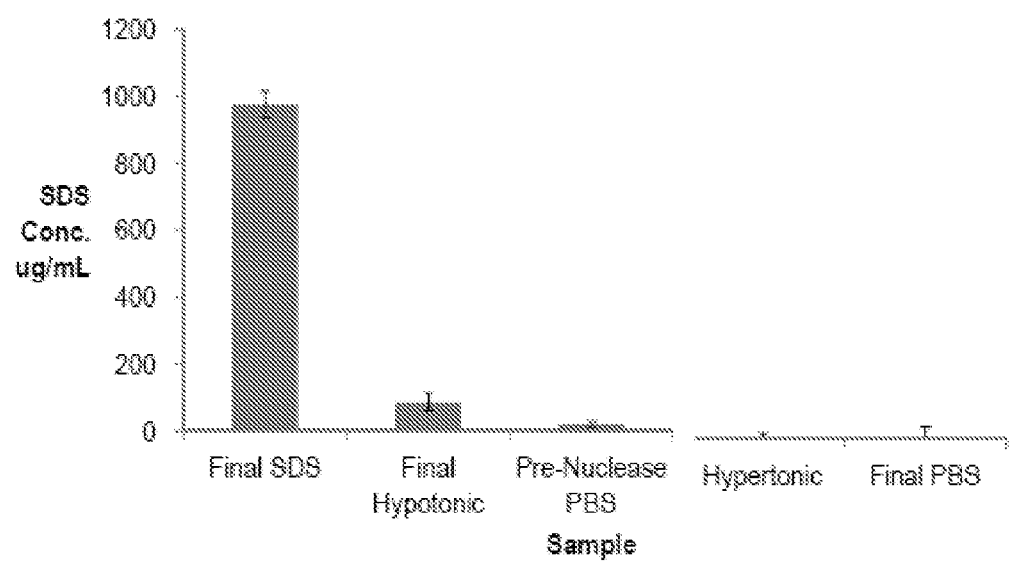
FIGS. 11A and 11B shows the residual sodium dodecyl sulfate (SDS) content of decellularised bone-meniscus-bone.
Figure 11:
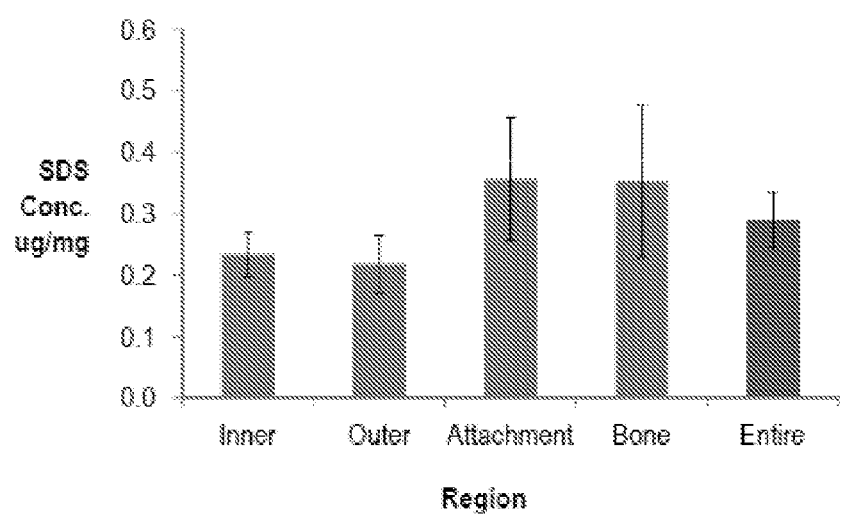

The SDS content of decellularised BMB was assessed using $C^{14}$ SDS assay (FIGS. 11A and 11B). The cytotoxity limit of SDS cited in the literature is around 10 μg/mg of tissue. Results showed that in samples the SDS concentration of SDS μg/mg was well below the toxic levels indicating that BMBs produced by the methods of the present invention are non-toxic.

Example 8

Figure 12:
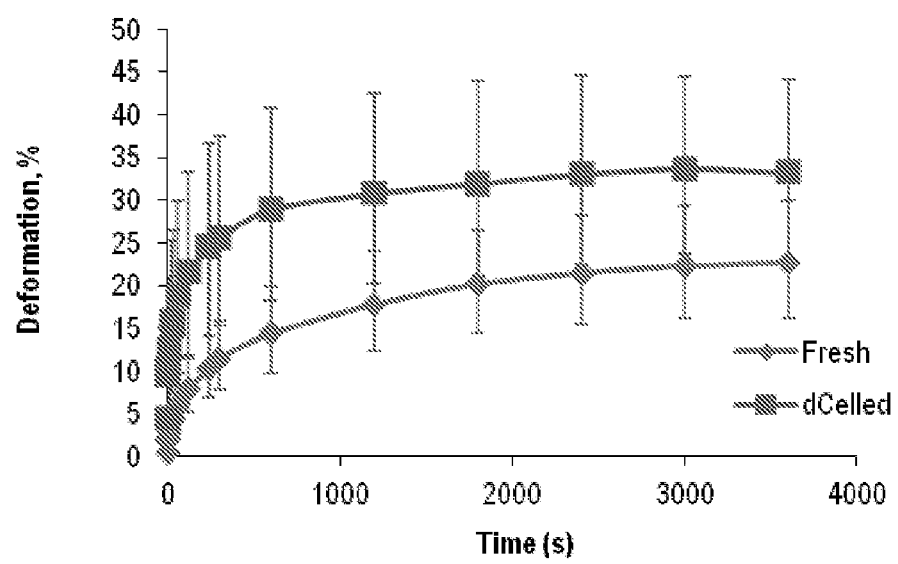
FIG. 12 shows deformation under load for native and decellularised bone-meniscus-bone implants.

The deformation under load for native and decellularised BMB was assessed using an indentation test where samples (n=5) taken from the central portion of the meniscus were loaded using a 2 mm flat indenter for an hour and the displacement measured (FIG. 12). These results were then fed into a finite element model to determine the Young's modulus and permeability of the samples. A Young's modulus of 0.178 MPa was obtained for decellularised meniscus compared to 0.205 MPa for native meniscus, suggesting native meniscus was not significantly stiffer than the decellularised meniscus (p>0.05).

In conclusion, the methods of the present invention have successfully been developed to decellularised bone-connective tissue-bone implants/scaffolds. Moreover, such scaffolds have been histologically, structurally and immunohistologically characterised to be of comparable equivalence of natural/native tissue.

Example 9

Figure 13A:
FIG. 13 shows DAPI staining of fresh (FIG. 13A) and decellularised osteochondral porcine tissue prepared by the methods of the present invention (FIG. 13B).
Figure 13B:
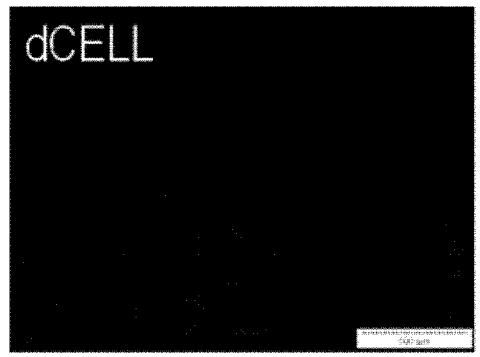
Figure 14A:
FIG. 14 shows DAPI staining of fresh (FIG. 14A) and osteochondral bovine tissue prepared by the methods of the present invention (FIG. 14B).
Figure 14B:
Figure 15A:
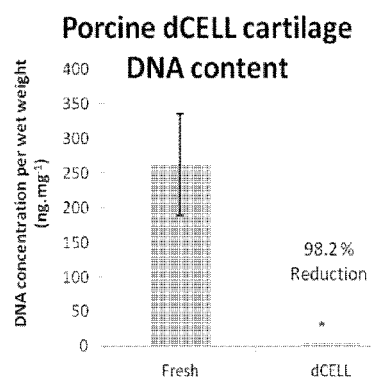
FIG. 15 shows DNA content of porcine (FIG. 15A) and bovine (FIG. 15B) fresh and dCELL cartilage.
Figure 15B:
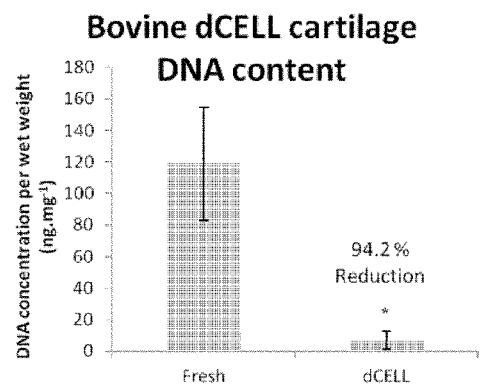

DAPI staining of fresh (FIG. 13A) and porcine osteochondral tissue prepared by the methods of the present invention (FIG. 13B) and fresh (FIG. 14A) and bovine osteochondral tissue prepared by the methods of the present invention (FIG. 14B) resulted in cell nuclei being present in the fresh tissue but a complete removal of nuclei from the cartilage and subchondral bone following decellularisation. The DNA content of porcine (FIG. 15A) and bovine (FIG. 15B) fresh and decellularised cartilage, expressed as the mean (n=3)±95% confidence intervals, * significant, p<0.05 is shown in the bar charts. FIG. 15A shows a 98.2% reduction in porcine cartilage DNA following dCELL and FIG. 15B a 4.2% reduction in bovine cartilage DNA. DNA content of both porcine and bovine decellularised (dCELL) cartilage falls below 50 ng·mg$^{-1}$ per tissue try weight, so both scaffolds are within specified criteria for decellularised tissue set by Crapo et al. (2011).

Example 10

Figure 16A:
FIG. 16 shows Alcian blue staining of fresh (FIG. 16A) and dCELL (FIG. 16B) porcine osteochondral tissues.
Figure 16B:
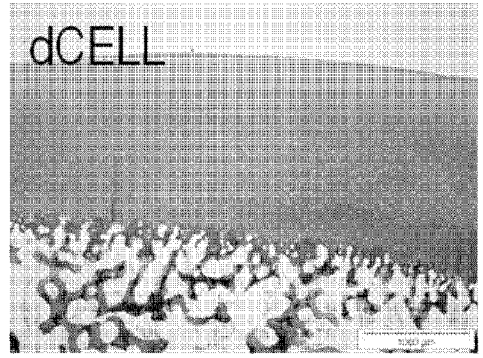
Figure 17A:
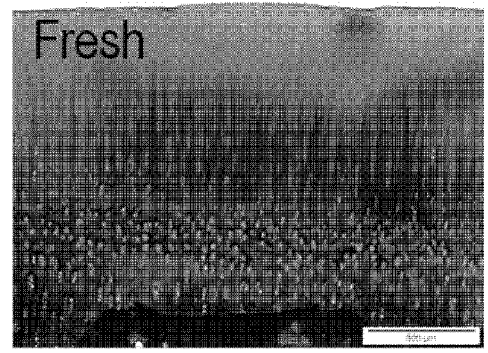
FIG. 17 shows Alcian blue staining of fresh (FIG. 17A) and dCELL (FIG. 17B) bovine osteochondral tissues.
Figure 17B:
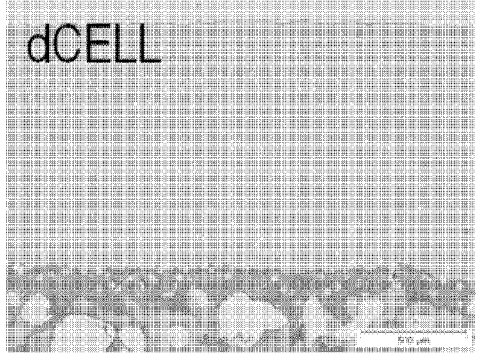
Figure 18A:
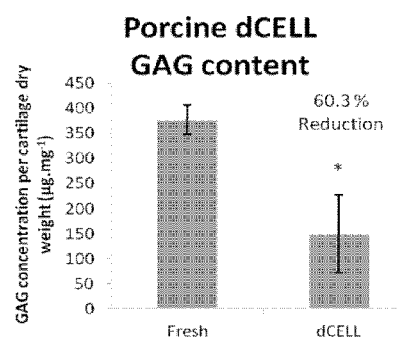
FIG. 18 shows GAG content of porcine (FIG. 18A) and bovine (FIG. 18B) fresh and dCELL cartilage.
Figure 18B:
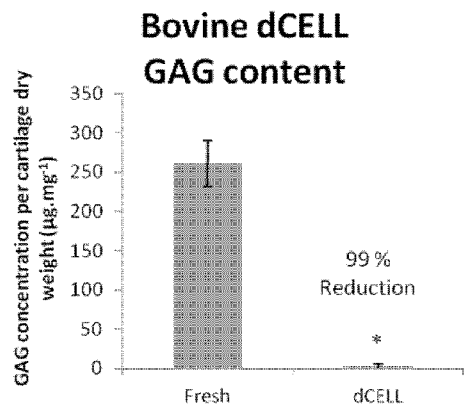

Alcian blue staining of fresh (FIG. 16A) and dCELL (FIG. 16B) porcine osteochondral tissues resulted in the fresh tissue showing intense staining for sulphated proteoglycans in fresh porcine tissue, especially in the middle zone of the cartilage. Intensity of staining is reduced in dCELL porcine tissue (FIG. 16B), suggesting loss of GAGs during the decellularisation process. The same reduction of Alcian blue staining is observed with fresh (FIG. 17A) and dCELL (FIG. 17B) bovine osteochondral tissues, again suggesting a large loss of GAGs during the decellularisation process. FIG. 18 shows GAG content of porcine (FIG. 18A) and bovine (FIG. 18B) fresh and dCELL cartilage. Data is expressed as the mean (Fresh n=5, dCELL n=3)±95% confidence intervals. * significant, p<0.05. FIG. 18A shows a 60.3% reduction in GAG content of porcine cartilage following decellularisation where as bovine cartilage shows almost complete GAG loss with a 99% reduction following decellularisation (FIG. 18B).

Figure 19A:
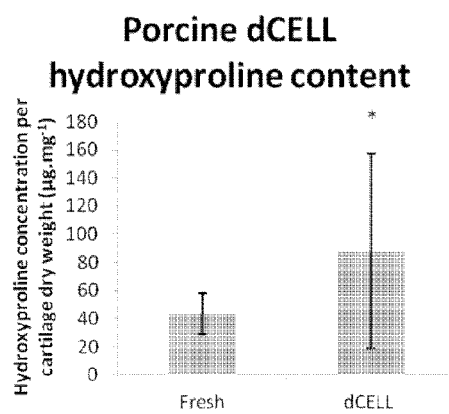
FIG. 19 shows hydroxyproline content of porcine (FIG. 19A) and bovine (FIG. 19B) fresh and dCELL cartilage.
Figure 19B:
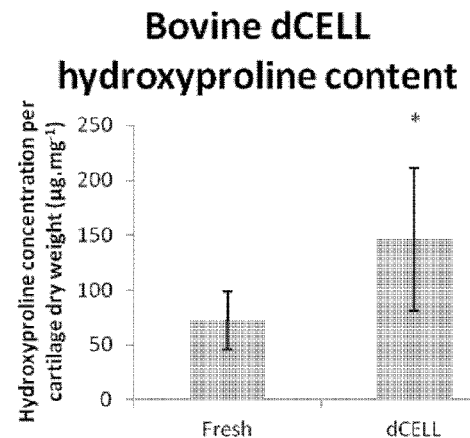

FIG. 19 shows hydroxyproline content of porcine (FIG. 19A) and bovine (FIG. 19B) fresh and dCELL cartilage. Data is expressed as the mean (Fresh n=5, dCELL n=3) ±95% confidence intervals. * significant, p<0.05. FIG. 19 shows a significant increase in hydroxyproline content of both porcine and bovine cartilage following decellularisation. Hydroxyproline content is given as a proportion of tissue dry weight. The dCELL process removes cells and other structural components (eg. GAGs) of the cartilage, therefore collagen will make up a higher proportion of tissue dry weight.

Example 11

Figure 20A:
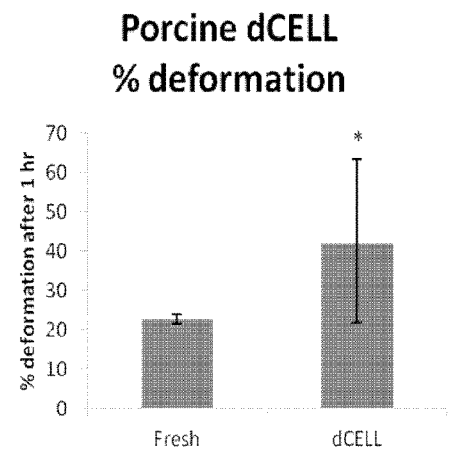
FIG. 20 shows the percentage deformation of fresh (FIG. 20A) and dCELL porcine (FIG. 20B) and bovine cartilage.
Figure 20B:
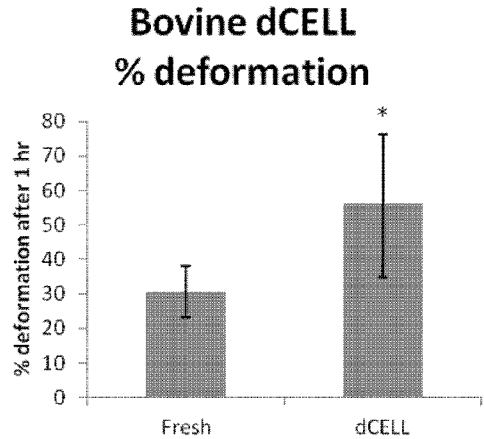

Compressive testing using an indenter was conducted. Osteochondral plugs (fresh n=5, dCELL n=3) were compressed in a purpose built indentation rig using a 3 mm diameter, hemispherical, stainless steel indenter under a load of 0.8 N. Plugs were submerged in PBS during testing to maintain cartilage hydration. The deformation of cartilage was measured at a sampling frequency of 5 Hz over one hour, after which all samples had reached equilibrium. Following compression, pins were fully rehydrated in PBS before cartilage thickness was measured. A needle indenter was used to penetrate the cartilage, lowering at a rate of 4.5 mm·min$^{-1}$; the resistance to motion was measured using a 500 N load cell [Instron 3365]. An increase in load was recorded when the needle first contacted the cartilage surface and a second increase when entering the bone, the distance between these two changes in load was taken as the cartilage thickness. Deformation of cartilage was normalised to thickness to give percentage deformation for each pin. FIG. 20 shows the percentage deformation of fresh (FIG. 20A) and dCELL porcine (FIG. 20B) and bovine cartilage. Data is expressed as the mean (Fresh n=5, dCELL n=3) ±95% confidence intervals. * significant, p<0.05. FIG. 20 shows a significant increase in the percentage deformation of both porcine and bovine cartilage following decellularisation. This is due to the loss of GAGs which act to hold fluid in the cartilage structure and resist compression according to the biphasic model of cartilage lubrication.

Example 12

Osteochondral grafts have been used to repair cartilage legions and, in turn restore joint function. However, there is limited understanding of the effect these grafts have on the local biotribology of the joint and their interactions with host tissue environment. It is postulated that following implantation of an osteochondral graft may change the biotribological and biomechanical function of the natural joint system may lead to degradation and wear on the opposing bearing surface, the osteochondral grafts or the cartilage adjacent to the grafts. The aim of this study was to establish whether osteochondral allografts and cartilage damage had an effect on the local biotribology post-implantation, in a simple tribological model of the natural joint.

A simple geometry multidirectional pin-on-plate tribological simulator was used to determine the coefficient of friction and degradation of bovine bone and cartilage plates (45 mm×19 mm×7 mm) sliding against 9 mm diameter bovine bone and cartilage pins. Osteochondral pins and plates were harvested from the patella groove of 18-24 month old skeletally mature cows. Intact osteochondral plates and pins (n=5) represented the negative control. Stainless steel pins inserted into 6 mm diameter defects in the plate were used as positive controls (n=5).

Test groups:
  Bovine allograft osteochondral grafts implanted into 6 mm defects in the bovine osteochondral plates (n=5)
  Ovine xenograft osteochondral grafts implanted into 6 mm defects in the bovine osteochondral plates (n=5)
  Porcine xenograft osteochondral grafts implanted into 6 mm defects in the bovine osteochondral plates (n=5)
  Decellularised Bovine allograft osteochondral grafts implanted into 6 mm defects in the bovine osteochondral plates (n=5)
  Decellularised Ovine xenograft osteochondral grafts implanted into 6 mm defects in the bovine ostoechondral plates (n=5)
  Decellularised Porcine xenograft osteochondral grafts implanted into 6 mm defects in the bovine osteochondral plates (n=5)

Tests were performed in phosphate buffered saline plus 25% (v/v) newborn calf serum. A stroke length of 20 mm was used with a velocity of 4 mm/s. A load of 160 N was applied to represent a physiological contact pressure of 2.5 MPa for a period of 6 h. The motion of the simulator produced a time dependent stress on the plate and osteochondral graft.

Figure 21:
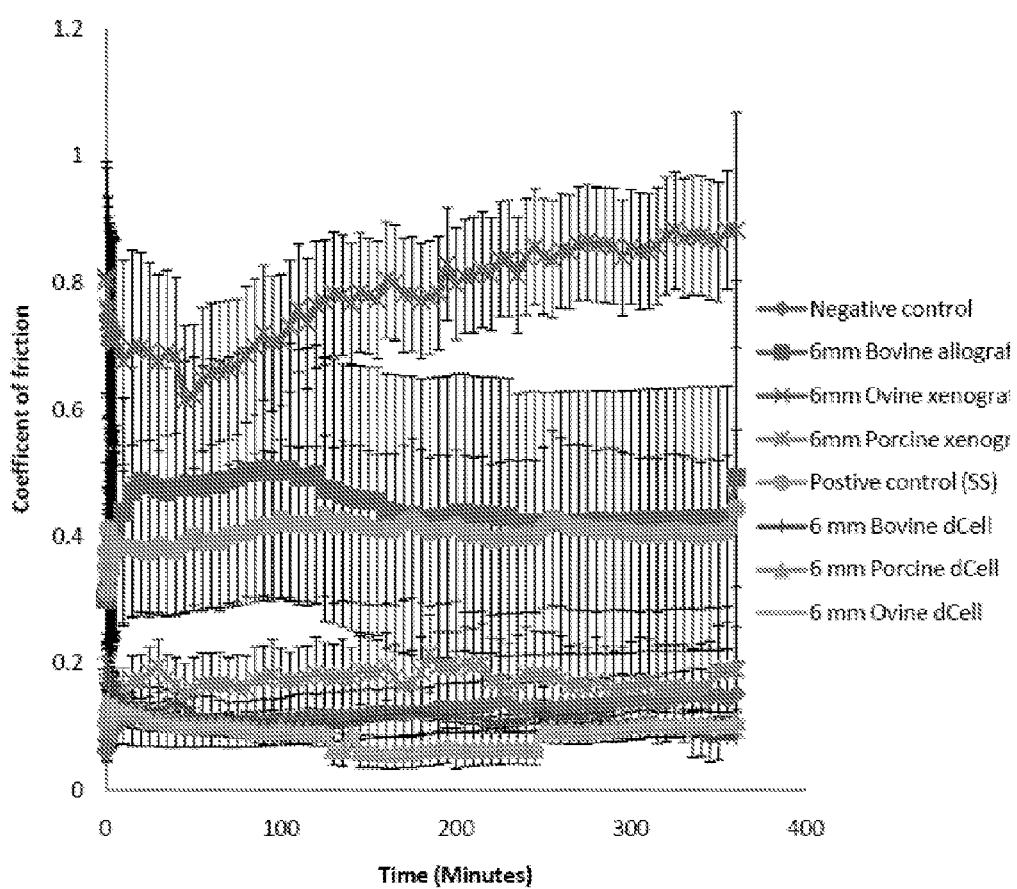
FIG. 21 shows coefficient of friction for decellularised and fresh bovine, ovine and porcine osteochondral plugs.
Figure 22:
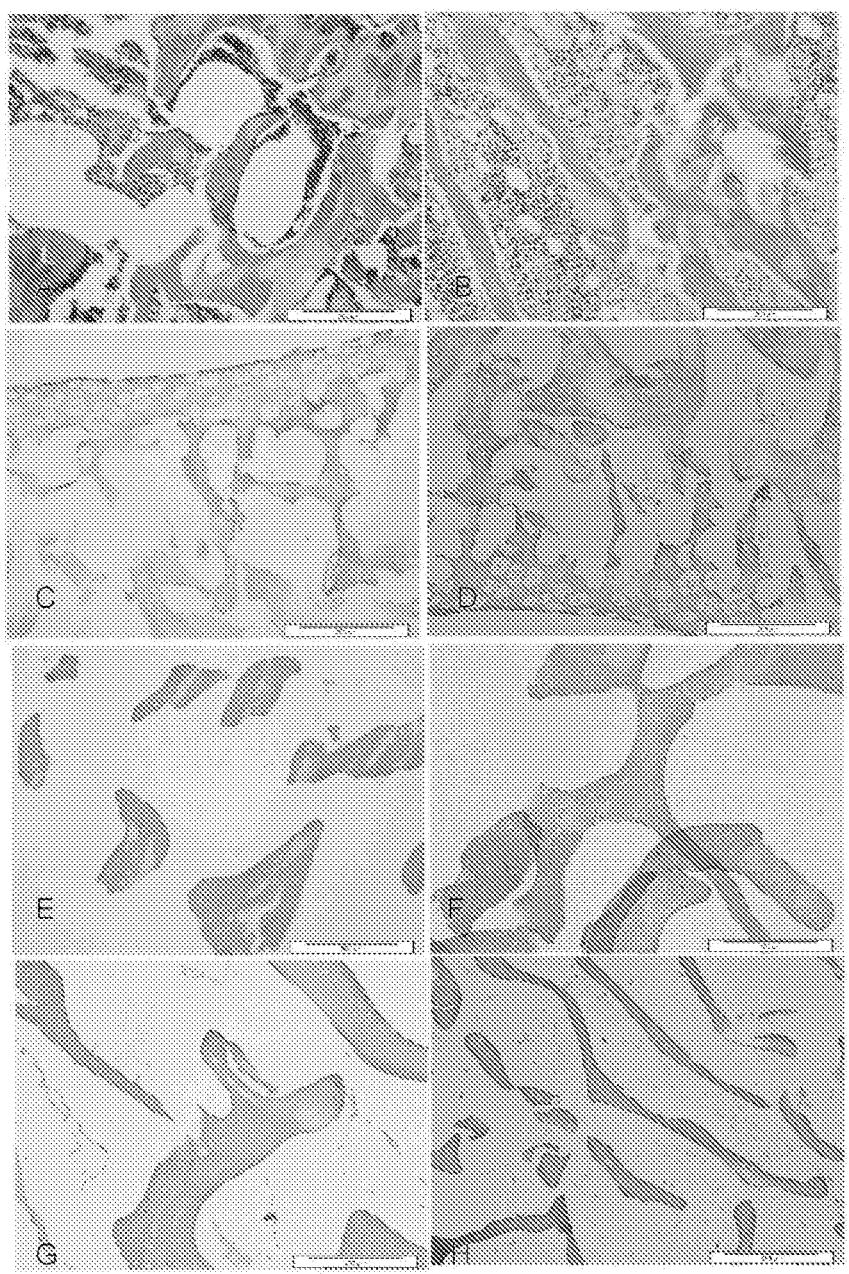
FIG. 22 shows bone plugs stained with Haematoxylin and Eosin, A) Fresh bone plug section 1, B) Fresh bone plug section 20 C) decell plug 1, section 1, D) decell plug 1, section 20, E) decell plug 2, section 1, E) decell plug 2, section 20. G) decell plug 3, section 1, H) decell plug 3, section 20.
Figure 27:
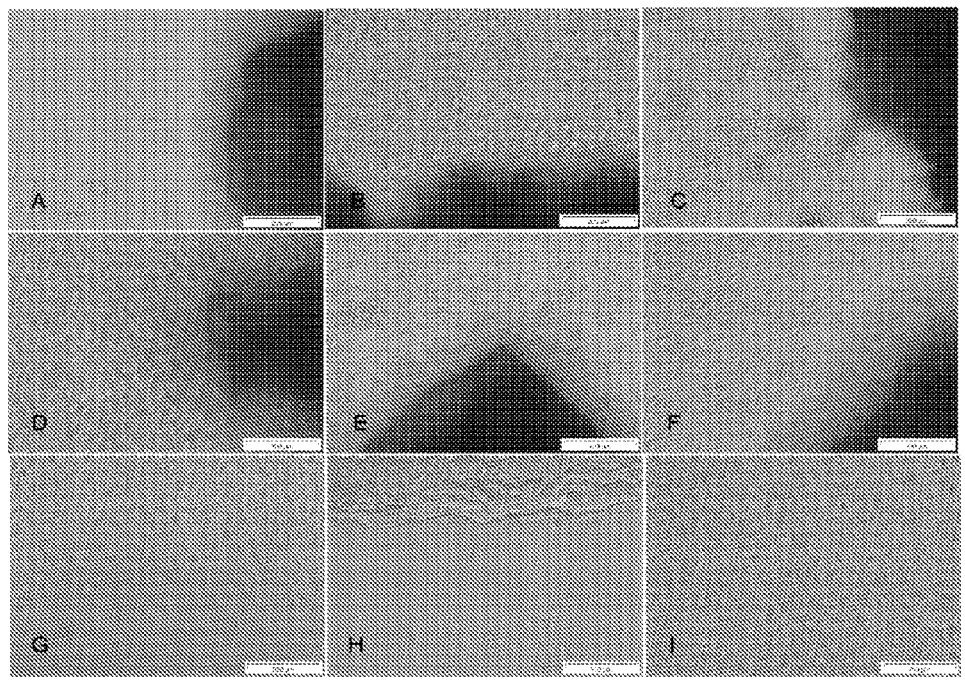
FIG. 27 shows contact cytotoxicity with 3T3 cells. 3T3 cells cultured with A) Fresh bone plug 1, B) Fresh bone plug 2, C) Fresh bone plug 3, D) Decell bone plug 1, E) Decell bone plug 2, F) Decell bone plug 3, G) Collagen control H) Glue positive control, I) Cells only control

The results are shown in FIG. 21). The negative control (n=5) exhibited a friction coefficient below 0.2 throughout the 6 h test period (FIG. 27). The positive control (n=5) showed a significantly higher coefficient of friction (p<0.05 ANOVA) compared to the negative control. The bovine allografts (n=5) showed a significantly higher coefficient of friction (p<0.05 ANOVA) compared to the negative control. When an ovine plug was inserted into the centre of a bovine plate the friction increased significantly compared to the other tests. However, inserting a porcine plug into the centre of plates showed the friction was not dissimilar to that of the negative control. This suggested that the mechanical properties of the porcine tissue may have contributed to the low coefficient of friction. The coefficient of friction for the decellularised bovine, ovine and porcine plug (inserted into plates) were similar to that of the negative control and the porcine xenograft. This suggested that the mechanical properties of the decellularised tissues were lower than the allograft and the ovine xenograft tissue and therefore, contributed to the low friction values.

Example 13

Bone plugs were stained with Haematoxylin and Eosin, A) Fresh bone plug section 1, B) Fresh bone plug section 20

Figure 23:
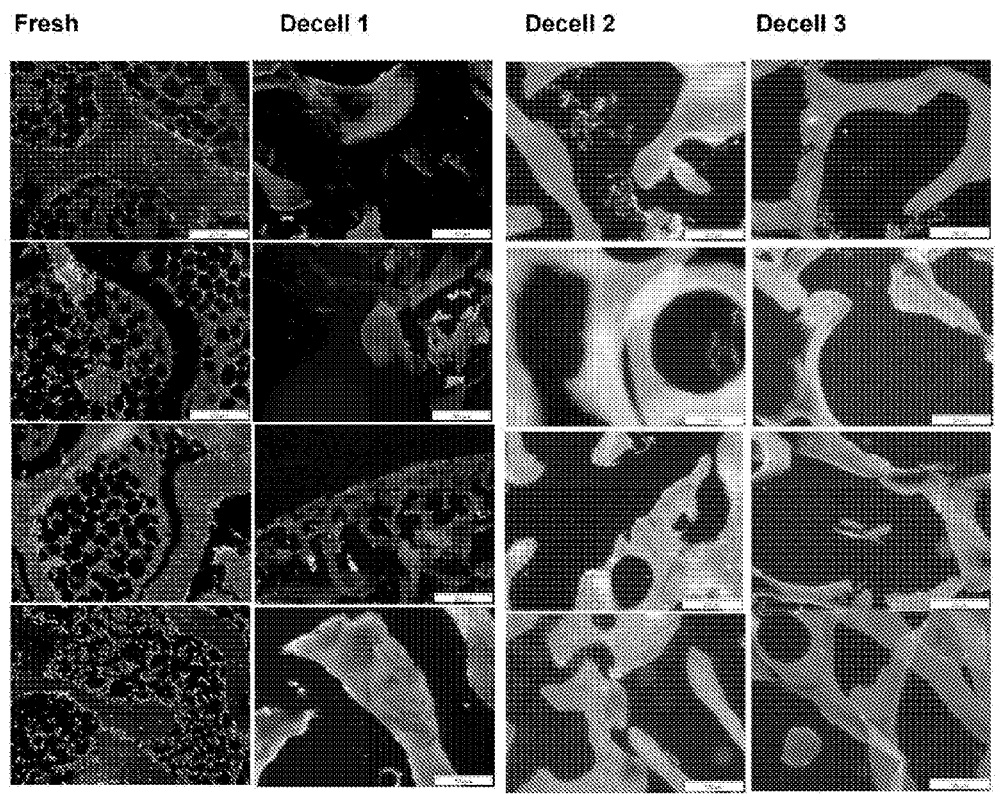
FIG. 23 shows Dapi staining of fresh and decellularised bone.

C) decell plug 1, section 1, D) decell plug 1, section 20, E) decell plug 2, section 1, E) decell plug 2, section 20. G) decell plug 3, section 1, H) decell plug 3, section 20. The H&E staining showed matrix stained pink and cell nuclei stained blue. The images show that the decellularisation process was successful in removing nuclei from the bone and from the bone marrow cavity (C-H) when compared to fresh bone (A-B). This was consistent throughout the plugs as shown by sections taken from the cut middle section (section 1) and centre of block (section 20) of the bone. Images C and D show that the cells were removed from the subchondral area of bone. FIG. 23 shows Dapi staining of fresh and decellularised bone. Images [top of panel] start from the centre of the plug [cut edge] and work into the block. The decellularised bone was clearly free from whole cells, as demonstrated by the lack of nuclei, however there appeared to be a small amount of debris present within the bone marrow cavity. This did not change throughout the different levels of sections.

Figure 24:
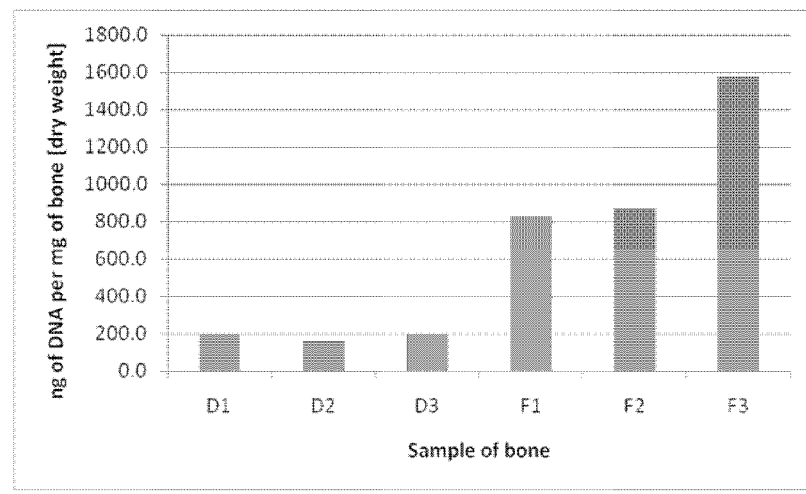
FIG. 24 shows the amount of DNA ng/mg of fresh and decellularised bone samples (dry weight).
Figure 25:
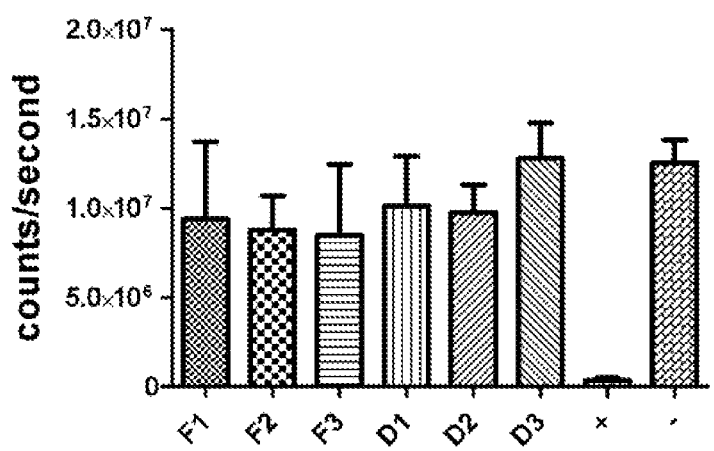
FIG. 25 shows extract cytotoxicity assay of fresh and decellularised bone plugs with BHK cells. F1-F3; fresh bone. D1-D3 decellularised bone; + Positive control DMSO; − Cells only Data is expressed as the mean [n=3] cps [ATP assay]±95% confidence intervals.
Figure 26:
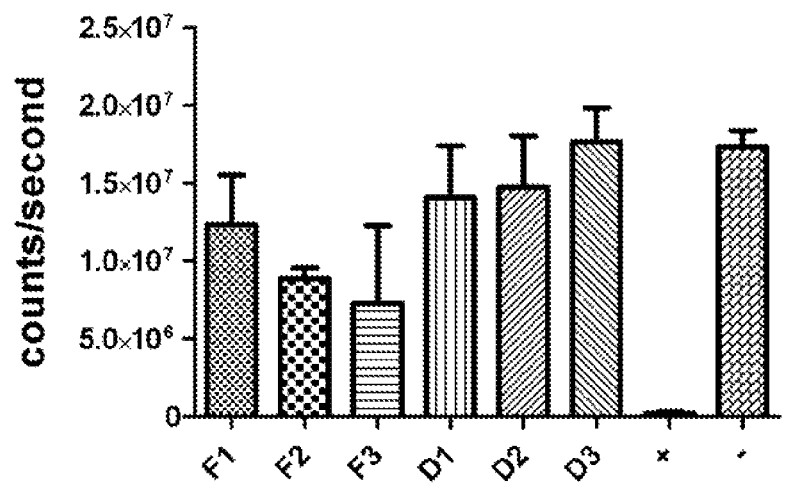
FIG. 26 shows extract cytotoxicity assay of fresh and decellularised bone plugs with 3T3 cells. F1-F3; fresh bone. D1-D3 decellularised bone; + Positive control DMSO; − Cells only Data is expressed as the mean [n=3] cps [ATP assay]±95% confidence intervals.

The amount of DNA ng/mg of fresh and decellularised bone samples (dry weight) is shown in FIG. 24 indicating a substantial reduction in decellularised bone as compared to fresh samples. FIG. 25 shows extract cytotoxicity assay of fresh and decellularised bone plugs with BHK cells. F1-F3; fresh bone. D1-D3 decellularised bone; + Positive control DMSO; − Cells only. Data is expressed as the mean [n=3] cps [ATP assay]±95% confidence intervals. FIG. 26 shows extract cytotoxicity assay of fresh and decellularised bone plugs with 3T3 cells. Extract cytotoxicity was performed with both fresh and decellularised bone plugs to determine their biocompatibility. The positive control [DMSO] showed a marked reduction in cell viability of both BHK (FIG. 25) and 3T3 (FIG. 26) cells at 48 h. The extracts from the decellularised bone plugs had no significant effect on the growth of BHK or 3T3 cells compared to the negative control [−; no extract]. The extracts of the fresh bone plugs had no significant effect on the growth of the BHK cells, but significantly reduced the growth of 3T3 cells over a 48 hour period.

Example 14

Contact cytoxicity assay was used to determine the biocompatibility of the bone. Small samples of bone were cultured in contact with baby hamster kidney (BHK) cells and the murine 3T3 cells for 48 hours. Collagen type 1 was used as a negative control [no contact inhibition] and cyanoacrylate contact adhesive as a positive control [contact inhibition]. The samples were examined using phase contrast microscopy before being fixed with NBF and then stained with Giemsa solution, washed and viewed using light microscopy.

Extract cytotoxicity Samples of bone were macerated and incubated with agitation and DMEM medium for 72 hours at 37° C. The sterility of the medium was checked by streaking onto various agar plates. BHK and 3T3 cells were seeded into 96 well plates and cultured for 24 hours, prior to addition of the extract media. DMSO was used as a positive control [reduced cell growth] and standard culture medium as a negative control [normal cell growth]. The extract medium was cultured for a further 48 hours before cell viability was analysed using the ATP lite assay and reading the luminescence using a Top-Count luminescence reader. Results were analysed using graph pad.

Figure 28:
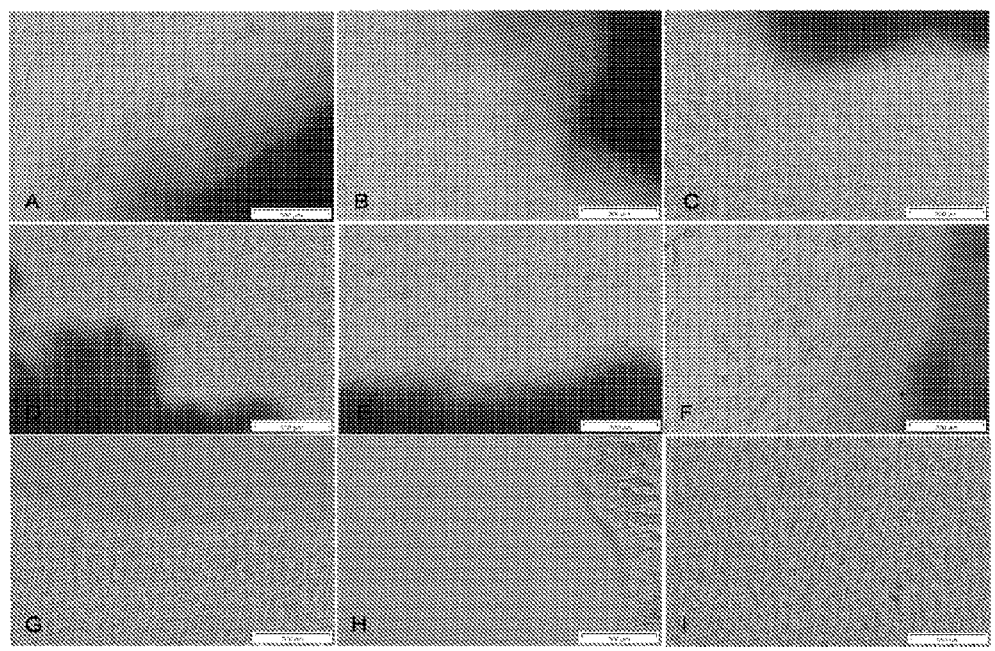
FIG. 28 shows contact cytotoxicity with BHK cells. BHK cells cultured with A) Fresh bone plug 1, B) Fresh bone plug 2, C) Fresh bone plug 3, D) Decell bone plug 1, E) Decell bone plug 2, F) Decell bone plug 3, G) Collagen control H) Glue positive control, I) Cells only control.

FIG. 27 shows contact cytotoxicity with 3T3 cells and FIG. 28 shows contact cytotoxicity with BHK cells. 3T3/BHK cells cultured with A) Fresh bone plug 1, B) Fresh bone plug 2, C) Fresh bone plug 3, D) Decell bone plug 1, E) Decell bone plug 2, F) Decell bone plug 3, G) Collagen control H) Glue positive control, I) Cells only control. The images (phase contrast microscopy) in FIGS. (27) and (28) show that both cell types [BHK and 3T3] were contact inhibited by the cyanoacrylate glue positive control but grew up to an in contact with the negative control [Collagen]. Both cell types [BHK and 3T3] grew up to the decellularised bone samples without any inhibition. Some cytotoxicity was visible in the fresh samples with both cell types, which may have been as a result of necrosis of the bone/bone marrow. The data overall showed that the decellularised bone plugs were biocompatible.

Example 14

Implantation into sheep condyles [in vitro] and micro-CT analysis was studied. Three Suffolk ovine (1 yr old) hind legs were dissected in order to expose the condyles. In the lateral side of each ovine condyle, two 6 mm diameter holes were drilled. These holes represented the defects in which, the porcine bone plugs [N=6] were inserted to congruency. The ovine femurs were scanned in an Xtreme microCT at a standard resolution.

An instron compression tester was used to determine the force required to push out the control and decellularised porcine bone specimens from the ovine condyles. The condyles were separated by cutting down the centre of the trochlea and femoral shaft. The femoral shaft was cemented into a custom-made fixture (using PMMA), leaving the condyles exposed before being fitted onto the Instron. A 5.5 mm indenter was used to push the bone plugs at a rate of 1 mm/min

TABLE 1

Initial force required to push the control and decellularised bone plugs out of the ovine condyles

| Type of bone plug | Load (N) | Mean ± 95% CL | Extension (mm) | Mean ± 95% CL |
|---|---|---|---|---|
| Control porcine (1) | 18.57 | 34.58 ± 15.63 | 0.79 | 1.31 ± 0.39 |
| Control porcine (2) | 34.47 | | 1.60 | |
| Control porcine (3) | 25.63 | | 1.25 | |
| Control porcine (4) | 46.88 | | 1.73 | |
| Control porcine (5) | 24.56 | | 0.99 | |
| Control porcine (6) | 57.40 | | 1.51 | |
| Decell porcine (1) | 8.80 | 11.73 ± 7.55 | 3.00 | 3.13 ± 0.12 |
| Decell porcine (2) | 8.86 | | 3.18 | |
| Decell porcine (3) | 6.95 | | 3.28 | |
| Decell porcine (4) | 25.62 | | 3.15 | |
| Decell porcine (5) | 6.85 | | 3.20 | |
| Decell porcine (6) | 13.28 | | 3.02 | |

The initial force to push out the control porcine bone plugs was significantly higher than the initial force to push out the decellularised porcine plugs (P<0.05; Student's t-test). The increased extension rate (P<0.05; Student's t-test) for the decellularised bone plugs compared to the control bone plugs indicated that the decellularised bone plugs were more compressible and compressed more than the control plugs before the initial plug movement.

Example 15

Figure 32:
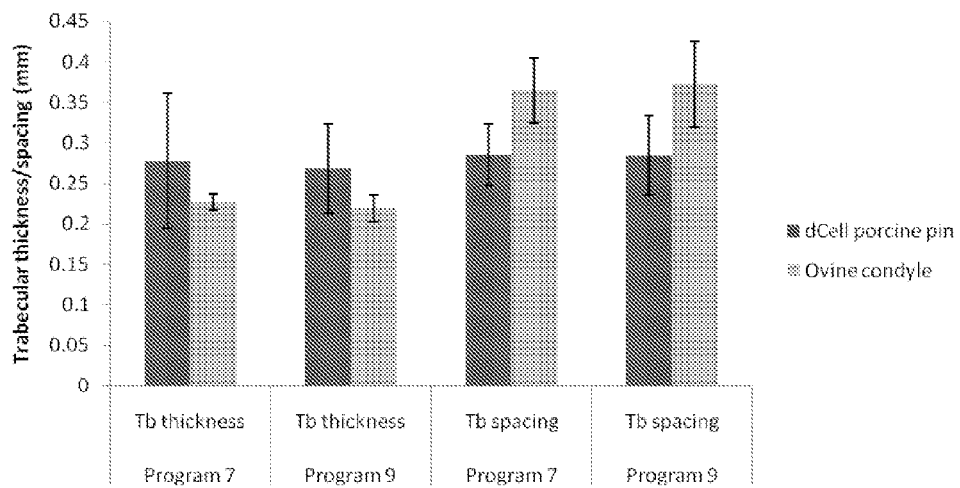
FIG. 32 shows mean trabecular thickness and spacing of decellularised porcine pins and ovine condyles Data is presented as the mean (n=6)±95% confidence limits.

Three Suffolk ovine (1 yr old) hind legs were dissected in order to expose the condyles. In the lateral side of each ovine condyle, two 6 mm diameter holes were drilled. These holes represented the defects in which, the porcine bone plugs [N=6] were inserted to congruency. The ovine femurs were scanned in an Xtreme microCT at a standard resolution. Two representative images show a control bone plug (FIG. 29) and a decellularised bone plug (FIG. 30) implanted into condyles. The bone was analysed using the micro-CT software (Scan IP) using two programs (program 7 and program 8) to determine the trabecular thickness and spacing. The bone of the host tissue (ovine condyle) adjacent to the control and decellularised bone plugs was analysed, as well as the bone plugs themselves. The average trabecular thickness and spacing of the ovine condyles and the bone plugs is shown in FIGS. (31) and (32). FIG. 31 shows mean trabecular thickness and spacing of control porcine pins and ovine condyles. Data is presented as the mean (n=6)±95% confidence limits. There were no significant differences between program 7 and 9. The trabecular thickness and spacing of the ovine condyles were slightly higher than but not significantly to the control porcine plugs. FIG. 32 shows mean trabecular thickness and spacing of decellularised porcine pins and ovine condyles Data is presented as the mean (n=6)±95% confidence limits. Program 7 refers to the analysis which takes into account the bone marrow, whereas Program 9 refers to analysis which does not take the bone marrow into account. There were no significant differences between program 7 and 9. The trabecular thickness of the decellularised porcine plugs was slightly lower than (but not significantly) the ovine condyles. The trabecular spacing within the ovine condyle bone was higher than (but not significantly) the decellularised bone plugs.

Figure 33:
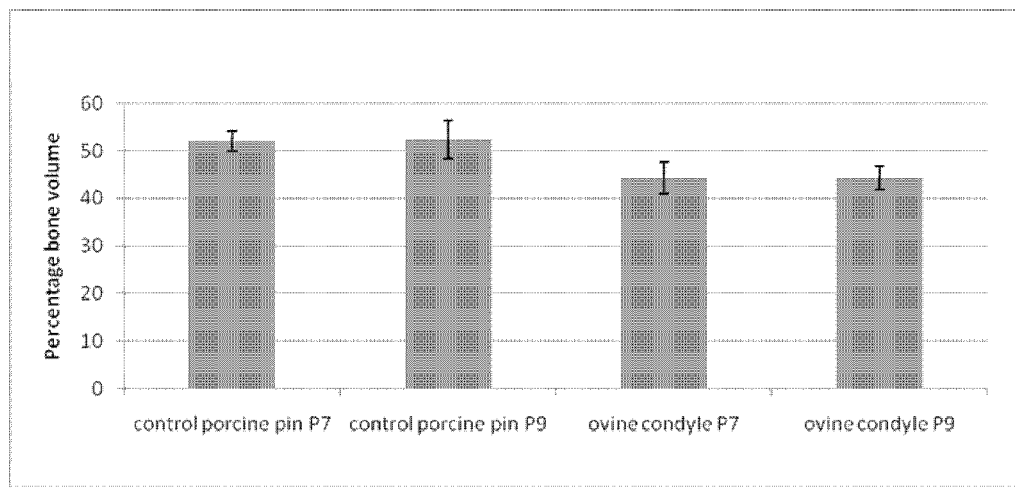
FIG. 33 shows the percentage bone volume of control porcine bone plugs and ovine condyles.
Figure 34:
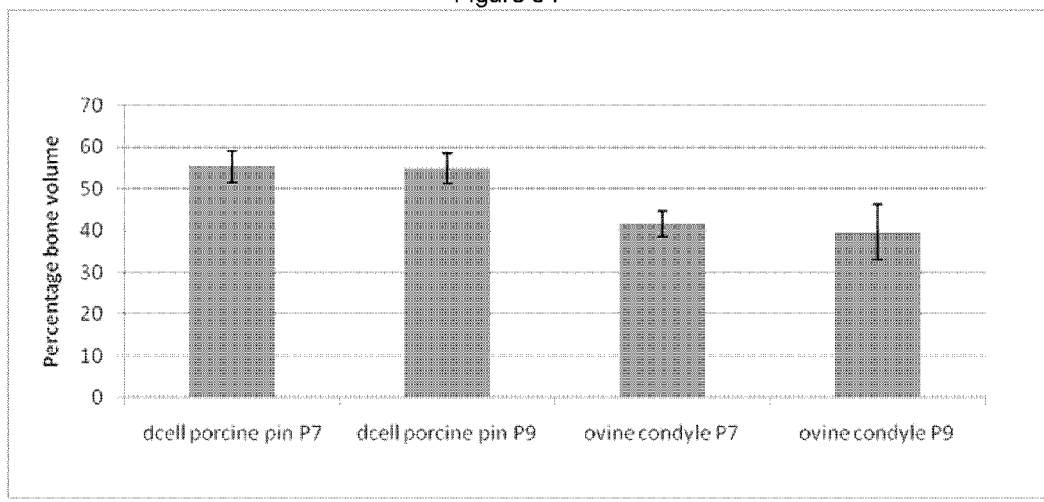
FIG. 34 shows the percentage bone volume of control porcine bone plugs and ovine condyles. Data is presented as the mean (n=6)±95% confidence limits

The percentage bone volume was determined for the control porcine bone plugs (program 7 and 9) and the adjacent ovine condyle (FIG. 33) and the decellularised bone plugs and adjacent ovine condyle (FIG. 34). FIG. 33 shows the percentage bone volume of control porcine bone plugs and ovine condyles. Data is presented as the mean (n=6)±95% confidence limits. The bone volume between the ovine condyles was less than the control porcine plugs (for either analysis program). FIG. 34 shows the percentage bone volume of control porcine bone plugs and ovine condyles. Data is presented as the mean (n=6)±95% confidence limits. The bone volume for ovine condyles was less than the decellularised porcine plugs (for either analysis program). There was no significant difference in the bone volume between the control porcine bone plugs (FIGS. 33 and 34) and the decellularised porcine bone plugs In conclusion, the methods of the present invention have successfully been developed to decellularised osteochondral tissue-bone implants/scaffolds. Moreover, such scaffolds have been histologically, structurally and immunohistologically characterised to be of comparable equivalence of natural/native tissue.

The invention claimed is:
1. A product comprising a decellularised natural multi-composite bone transplant material characterised by the absence or substantial absence of cells in the whole composite, wherein the multi-composite bone transplant material is bone-connective tissue-bone or osteochondral, wherein the substantial absence is between 90% and up to 100% removal of cells from all parts of the multi-composite transplant product.
2. The product according to claim 1 that retains its original histoarchitecture and structural collagen composition as compared to a native fresh cellularised counterpart composite tissue.

3. The product according to claim 1, wherein total genomic DNA (gDNA) content of all tissue types in the multi-composite product is between 0 to 10% of the native tissue.

4. The product according to claim 1 that is derived from allogenic tissue.

5. The product according to claim 1 that is derived from xenogeneic tissue selected from the group consisting of porcine, bovine or ovine tissue.

6. The product according to claim 1, wherein the connective tissue is selected from the group consisting of ligaments, meniscus and enthesis.

7. The product according to claim 6, wherein the ligaments are selected from the group consisting of head and neck ligaments, wrist and finger ligaments, knee ligaments, thorax ligaments, foot ligaments and pelvis ligaments.

8. The product according to claim 7, wherein the knee ligaments are selected from the group consisting of anterior cruciate ligament (ACL), lateral collateral ligament (LCL), posterior cruciate ligament (PCL), medial collateral ligament (MCL), cranial cruciate ligament (CRCL)—quadruped equivalent of ACL, caudal eructate ligament (CACL)—quadruped equivalent of PCL and patellar ligament.

9. The product according to claim 6, wherein the meniscus is medial meniscus tissue and the medial meniscus tissue includes attachment tissue or enthesis at either end of the meniscus attaching the meniscus to each terminal bone block.

10. A method of treatment of an individual requiring knee repair or replacement surgery comprising replacing a defective or damaged knee joint with the product comprising a decellularised natural multi-composite bone transplant material of claim 1.

11. A method of treatment of an individual requiring patella tendon knee repair or replacement surgery comprising replacing a defective or damaged area with the product comprising a decellularised natural multi-composite bone transplant material of claim 1.

12. A method of treatment of an individual requiring osteochondral repair or replacement surgery comprising replacing a defective or damaged area with the product comprising a decellularised natural multi-composite bone transplant material of claim 1.

* * * * *